US010947239B2

(12) United States Patent
Buijnsters et al.

(10) Patent No.: US 10,947,239 B2
(45) Date of Patent: Mar. 16, 2021

(54) [1,2,4]TRIAZOLO[1,5-A]PYRIMIDIN-7-YL COMPOUND

(71) Applicant: Janssen Pharmaceutica NV, Beerse (BE)

(72) Inventors: Petrus Jacobus Johannes Antonius Buijnsters, Etten-Leur (NL); Henricus Jacobus Maria Gijsen, Breda (NL); Wilhelmus Helena Ignatius Maria Drinkenburg, Molenschot (NL); Abdallah Ahnaou, Sint-Lambrechts-Woluwe (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/772,859

(22) PCT Filed: Nov. 2, 2016

(86) PCT No.: PCT/EP2016/076420
§ 371 (c)(1),
(2) Date: May 2, 2018

(87) PCT Pub. No.: WO2017/076900
PCT Pub. Date: May 11, 2017

(65) Prior Publication Data
US 2018/0327408 A1 Nov. 15, 2018

(30) Foreign Application Priority Data

Nov. 2, 2015 (EP) ..................................... 15192661
Nov. 4, 2015 (EP) ..................................... 15192966

(51) Int. Cl.
| C07D 487/04 | (2006.01) |
| A61P 25/34 | (2006.01) |
| A61P 25/36 | (2006.01) |
| A61P 25/28 | (2006.01) |
| A61P 25/22 | (2006.01) |
| A61P 25/32 | (2006.01) |
| A61P 25/18 | (2006.01) |
| A61P 25/16 | (2006.01) |
| A61K 45/06 | (2006.01) |

(52) U.S. Cl.
CPC ............ *C07D 487/04* (2013.01); *A61P 25/16* (2018.01); *A61P 25/18* (2018.01); *A61P 25/22* (2018.01); *A61P 25/28* (2018.01); *A61P 25/32* (2018.01); *A61P 25/34* (2018.01); *A61P 25/36* (2018.01); *A61K 45/06* (2013.01); *A61K 2300/00* (2013.01)

(58) Field of Classification Search
CPC .................................................. C07D 487/04
See application file for complete search history.

(56) References Cited

U.S. PATENT DOCUMENTS

| 7,449,465 | B2 | 11/2008 | Freyne et al. |
| 8,138,168 | B1 | 3/2012 | Jones et al. |
| 8,946,415 | B2 | 2/2015 | Bi et al. |
| 9,682,953 | B2 | 6/2017 | Kharul et al. |
| 2004/0014744 | A1 | 1/2004 | Haviv et al. |
| 2009/0259044 | A1 | 10/2009 | Kazantsev |
| 2014/0031547 | A1 | 1/2014 | Sheridan et al. |

FOREIGN PATENT DOCUMENTS

| CA | 2979222 | 9/2016 |
| CN | 1938308 | 3/2007 |
| CN | 103958473 | 7/2014 |
| CN | 104302649 | 1/2015 |
| CN | 105566321 | 11/2016 |
| EP | 0941994 | 9/1999 |
| JP | 2007332061 | 12/2007 |
| JP | 2014503528 | 2/2014 |
| WO | WO 93/00313 | 7/1993 |
| WO | WO 99/37304 | 7/1999 |
| WO | WO 2004/031148 | 4/2004 |
| WO | WO 2004108136 | 12/2004 |
| WO | WO 2005/063738 | 7/2005 |
| WO | WO 2006/034341 | 3/2006 |
| WO | WO 2006/034440 | 3/2006 |
| WO | WO 2006044687 | 4/2006 |
| WO | WO 2007/022225 | 2/2007 |
| WO | WO 2007113136 | 10/2007 |
| WO | WO 2008/048914 | 4/2008 |

(Continued)

OTHER PUBLICATIONS

Knott, E.P., et al. "Phosphodiesterase Inhibitors as a Therapeutic Approach to Neuroprotection and Repair." International Journal of Molecular Sciences. (2017), vol. 18, Issue 696, pp. 1-38 of 38. (Year: 2017).*
"Schizophrenia." (Mar. 2015). Accessed Mar. 29, 2019. Available from: < https://www.nami.org/NAMI/media/NAMI-Media/Images/FactSheets/Schizophrenia-FS.pdf >. (Year: 2015).*
"Substance-induced psychotic disorder." (Oct. 2005). Accessed Mar. 29, 2019. Available from: < http://www.minddisorders.com/Py-Z/Substance-induced-psychotic-disorder.html > . (Year: 2005).*
Perugi, G., et al. "Diagnosis and Treatment of Agoraphobia with Panic Disorder." CNS Drugs. (2007), 21(9), pp. 741-764. (Year: 2007).*

(Continued)

*Primary Examiner* — Andrew D Kosar
*Assistant Examiner* — John S Kenyon
(74) *Attorney, Agent, or Firm* — Yuriy P. Stercho

(57) ABSTRACT

The present invention relates to a novel [1,2,4]triazolo[1,5-a]pyrimidin-yl derivative as inhibitor of phosphodiesterase 2 (PDE2). The invention is also directed to pharmaceutical compositions comprising the compound, to processes for preparing such compound and compositions, and to the use of such compound and compositions for the prevention and treatment of disorders in which PDE2 is involved, such as neurological and psychiatric disorders.

11 Claims, 9 Drawing Sheets

(56) References Cited

FOREIGN PATENT DOCUMENTS

| WO | WO 2009047514 | 4/2009 | | |
|---|---|---|---|---|
| WO | WO 2012/114222 | 8/2012 | | |
| WO | WO 2013/000924 | 1/2013 | | |
| WO | WO 2013134113 | 9/2013 | | |
| WO | WO 2015/130905 | 9/2015 | | |
| WO | WO 2015140055 | 9/2015 | | |
| WO | WO2015/164508 | 10/2015 | | |
| WO | WO-2015164508 A1 | * 10/2015 | ........... | C07D 487/04 |
| WO | WO 2016/107602 | 7/2016 | | |
| WO | WO 2017/003894 | 1/2017 | | |
| WO | WO 2017/003895 | 1/2017 | | |
| WO | WO 2017/066705 | 4/2017 | | |
| WO | WO 2017157882 | 9/2017 | | |
| WO | WO 2017/076900 | 11/2017 | | |
| WO | WO 2018/083098 | 5/2018 | | |
| WO | WO 2018/083101 | 5/2018 | | |
| WO | WO 2018/083103 | 5/2018 | | |
| WO | WO 2018109198 | 6/2018 | | |

OTHER PUBLICATIONS

Reisman, M. "PTSD Treatment for Veterans: What's Working, What's New, and What's Next." P&T. (Oct. 2016), vol. 41, No. 10, pp. 623-634. (Year: 2016).*
Alzheimer's Association. "Huntington's Disease." (2012). Accessed Mar. 29, 2019. Available from: < https://www.alz.org/alzheimers-dementia/what-is-dementia/types-of-dementia/huntington-s-disease >. (Year: 2012).*
Muller, N., et al. "Tourette's syndrome: clinical features, pathophysiology, and therapeutic approaches." Dialogues Clin Neurosci. (2007), vol. 9, pp. 161-171. (Year: 2007).*
Alzheimer's Association. "What Is Alzheimer's?" (Jan. 2007). Accessed Mar. 29, 2019. Available from: < https://www.alz.org/alzheimers-dementia/what-is-alzheimers >. (Year: 2007).*
National Institute of Environmental Health Sciences. "Parkinson's Disease." (Feb. 2014). Accessed Mar. 29, 2019. Available from: < https://www.niehs.nih.gov/health/topics/conditions/parkinson/index.cfm > . (Year: 2014).*
Sweeney, P. "Parkinson's disease." Cleveland Clinic. (May 2013). Accessed Mar. 29, 2019. Available from: < http://www.clevelandclinicmeded.com/medicalpubs/diseasemanagement/neurology/parkinsons-disease/ >. (Year: 2013).*
International Search Report re: PCT/EP2016/076420 dated Dec. 15, 2016.
International Search Report and Written Opinion—PCT/EP2017/077910.
International Search Report and Written Opinion—PCT/EP2017/077918.
International Search Report and Written Opinion—PCT/EP2017/077920.
Albensi et al. Exp Neurol. 2007, vol. 204A, pp. 1-13.
Barco et al., Expert Opin Ther Targets 2003, vol. 7, pp. 101-114.
Bergado and Almaguer Neural Plast. 2002, vol. 9, No. 4, pp. 217-232.
Buijnsters et al. "Structure-Based Design of a Potent, Selective, and Brain Penetrating PDE2 Inhibitor with Demonstrated Target Engagement" ACS Med Chem Lett. 2014, vol. 5(9), pp. 1049-1053.
Cooke and Bliss, Curr Opin Investig Drugs. 2005, vol. 6, No. 1, pp. 25-34.
Dyatkin A.B. et. al, Chirality 2002, vol. 14, pp. 215-219.
Francis et al. Physiol Rev. 2011, vol. 9, pp. 651-690.
Gomez Laurent et al. "PDE2 inhibition: Potential for the treatment of cognitive disorders" Bioorganic & Medicinal Chemistry Letters 2013, vol. 3, No. 24, pp. 6522-6527.
Lakics, V. et al. "Quantitative comparison of phosphodiesterase mRNA distribution in human brain and peripheral tissues" 2010 Neuropharmacol. vol. 59, pp. 367-374.
Omori and Kotera Circ Res. 2007, vol. 100, pp. 309-327.
Rowan et al. Biochem Soc Trans. 2005, vol. 33, pp. 563-567.
Su et al. Angew. Chem. Int. Ed. 2015, vol. 54, pp. 12942-12946.
Van Duinen et al., Curr Pharm Des. 2015, vol. 21, pp. 3813-3828.
Xu et al., Neurobiol Aging. 2015, vol. 36, pp. 955-970.
CAS 1240215-31-9, Sep. 8, 2010, Methanone, [5-[(diethylamino)methyl]-2-furanyl][3-[6-(methylsulfonyl)[1,2,4]triazolo[1,5-a]pyrimidin-7-yl]-1-piperidinyl].
CAS 1240208-98-3, Sep. 8, 2010, Methanone, (1,2-dimethyl-1H-benzimidazol-5-yl)[3-[6-(methylsulfonyl)[1,2,4]triazolo[1,5-a]pyrimidin-7-yl]-1-piperidinyl.
CAS 1240206-26-1, 08 Set 2010, 1-Piperidinecarboxylic acid, 3-[3-methyl-2-(3-methylphenyl)pyrazolo[1,5-a]pyrimidin-7-yl]-, 1,1-dimethylethyl ester.
CAS 1240201-99-3, Sep. 7, 2010, Benzoic acid, 4-[[3-[6-(methylsulfonyl)[1,2,4]triazolo[1,5-a]pyrimidin-7-yl]-1-piperidinyl]carbonyl]-, methyl ester.
CAS 1240195-90-7, Sep. 7, 2010, Methanone, (1,5-dimethyl-1H-pyrazol-4-yl)[3-[6-(methylsulfonyl)[1,2,4]triazolo[1,5-a]pyrimidin-7-yl]-1-piperidinyl].
CAS 1240195-65-6, Sep. 7, 2010, Methanone, [3-[6-(methylsulfonyl)[1,2,4]triazolo[1,5-a]pyrimidin-7-yl]-1-piperidinyl]-1H-pyrazol-3-yl.
CAS 1240193-46-7, Sep. 7, 2010, Methanone, [1-(4-methoxyphenyl)cyclopropyl][3-[6-(methylsulfonyl)[1,2,4]triazolo[1,5-a]pyrimidin-7-yl]-1-piperidinyl].
CAS 1240193-08-1, Sep. 7, 2010, 1-Piperidinecarboxylic acid, 3-[2-(3-methylphenyl)pyrazolo[1,5-a]pyrimidin-7-yl]-, 1,1-dimethylethyl ester.
CAS 1240192-13-5, Sep. 7, 2010, 1-Propanone, 3-(5-methyl-1H-pyrazol-1-yl)-1-[3-[6-(methylsulfonyl)[1,2,4]triazolo[1,5-a]pyrimidin-7-yl]-1-piperidinyl].
CAS 1240186-67-7, Sep. 7, 2010, 1-Propanone, 3-(1-ethyl-3,5-dimethyl-1H-pyrazol-4-yl)-1-[3-[6-(methylsulfonyl)[1,2,4]triazolo[1,5-a]pyrimidin-7-yl]-1-piperidinyl].
Cas 1240181-24-1, Sep. 7, 2010, Methanone, (5-methyl-1-propyl-1H-pyrazol-4-yl)[3-[6-(methylsulfonyl)[1,2,4]triazolo[1,5-a]pyrimidin-7-yl]-1-piperidinyl].
CAS 1240176-67-3, Sep. 7, 2010, 1-Butanone, 4-(1H-indol-3-yl)-1-[3-]6-(methylsulfonyl)[1,2,4]triazolo[1,5-a]pyrimidin-7-yl[-1-piperidinyl].
CAS 1240169-61-2, Sep. 7, 2010, Methanone, (1-ethyl-5-methyl-1H-pyrazol-4-yl)[3-[6-(methylsulfonyl)[1,2,4]triazolo[1,5-a]pyrimidin-7-yl]-1-piperidinyl].
CAS 1240169-40-7, Sep. 7, 2010, Ethanone, 2-(3,4-dimethoxyphenyl)-1-[3-[6-(methylsulfonyl)[1,2,4]triazolo[1,5-a]pyrimidin-7-yl]-1-piperidinyl].
CAS 1240166-99-7, Sep. 7, 2010, Methanone, [3-(1,1-dimethylethyl)-1-methyl-1H-pyrazol-5-yl][3-[6-(methylsulfonyl)[1,2,4]triazolo[1,5-a]pyrimidin-7-yl]-1-piperidinyl].
CAS 1240166-22-6, Sep. 7, 2010, Methanone, (2-methyl-1H-benzimidazol-6-yl)[3-[6-(methylsulfonyl)[1,2,4]triazolo[1,5-a]pyrimidin-7-yl]-1-piperidinyl].
CAS 1240165-13-2, Sep. 7, 2010, Methanone, [1-(4-chlorophenyl)cyclobutyl][3-[6-(methylsulfonyl)[1,2,4]triazolo[1,5-a]pyrimidin-7-yl]-1-piperidinyl].
CAS 1240153-22-3, Sep. 7, 2010, Methanone, (1-ethyl-3-methyl-1H-pyrazol-4-yl)[3-[6-(methylsulfonyl)[1,2,4]triazolo[1,5-a]pyrimidin-7-yl]-1-piperidinyl].
CAS 1240147-20-9, Sep. 7, 2010, 1-Piperidineacetamide, N-(3-ethoxpropyl)-3-[2-methyl-6-(3-methyl-5-isoxazoly)pyrazolo[1,5-a]pyrimidin-7-yl].
CAS 1240146-72-8, Sep. 7, 2010, Pyrimido[1,2-a]benzimidazole, 4-[1[[1-(2-propyn-1-yl)-1H-indol-3-yl]methyl]-3-piperidinyl].
CAS 1240140-89-9, Sep. 7, 2010, 1-Piperidinecarboxylic acid, 3-[2-(4-methylphenyl)pyrazolo[1,5-a]pyrimidin-7-yl]-, 1,1-dimethylethyl ester.
CAS 1240128-18-0, Sep. 7, 2010, Methanone, (3,4-dimethoxyphenyl)[3-[6-(methylsulfonyl)[1,2,4]triazolo[1,5-a]pyrimidin-7-yl]-1-piperidinyl].
CAS 1240127-92-7, Sep. 7, 2010, 1-Piperidinecarboxylic acid, 3-[2-(3-fluorophenyl)pyrazolo[1,5-a]pyrimidin-7-yl]-, 1,1-dimethylethyl ester.

(56) References Cited

OTHER PUBLICATIONS

CAS 1240115-42-7, Sep. 7, 2010, Methanone, (1-ethyl-1H-pyrazol-4-yl)[3-[6-(methylsulfonyl)[1,2,4]triazolo[1,5-a]pyrimidin-7-yl]-1-piperidinyl].
CAS 1240104-61-3, Sep. 7, 2010, 1-Piperidinecarboxylic acid, 3-(2-phenylpyrazolo[1,5-a]pyrimidin-7-yl)-,1,1-dimethylethyl ester.
CAS 1240102-95-7, Sep. 7, 2010, Methanone, [3-[6-(methylsulfonyl)[1,2,4]triazolo[1,5-a]pyrimidin-7-yl]-1-piperidinyl](4,5,6,7-tetrahydro-1H-indazol-3-yl).
CAS 1240096-26-7, Sep. 7, 2010, Ethanone, 2-(2,5-dimethoxyphenyl)-1[3-[6-(methylsulfonyl)[1,2,4]triazolo[1,5-a]pyrimidin-7-yl]-1-piperidinyl].
CAS 1240096-02-9, Sep. 7, 2010, 1-Piperidinecarboxylic acid, 3-[3-(4-fluorophenyl)-2-methylpyrazolo[1,5-a]pyrimidin-7-yl]-, 1,1-dimethylethyl ester.
CAS 1240093-87-1, Sep. 7, 2010, Methanone, (2,3-dihydro-1,4-benzodioxin-6-yl)[3-[6-(methylsulfonyl)[1,2,4]triazolo[1,5-a]pyrimidin-7-yl]-1-piperidinyl].
CAS 1240091-60-4, Sep. 7, 2010, Methanone, (4-amino-5-chloro-2-methoxyphenyl)[3-[6-(methylsulfonyl)[1,2,4]triazolo[1,5-a]pyrimidin-7-yl]-1-piperidinyl].
CAS 1214610-92-0, Mar. 25, 2010, Methanone, (3-methyl-2-benzofuranyl)[3-[6-(methylsulfonyl)[1,2,4]triazolo[1,5-a]pyrimidin-7-yl]-1-piperidinyl].
CAS 1214601-85-0, Mar. 25, 2010, Methanone, [3-[6-(methylsulfonyl)[1,2,4]triazolo[1,5-a]pyrimidin-7-yl]-1-piperidinyl](4-methyl-5-thiazolyl).
CAS 1214591-56-6, Mar. 25, 2010, Methanone, [3-[6-(methylsulfonyl)[1,2,4]triazolo[1,5-a]pyrimidin-7-yl]-1-piperidinyl](1,4,5,6-tetrahydro-3-cyclopentapyrazolyl).
CAS 1214520-74-7, Mar. 25, 2010, 1-Piperidineacetamide, N,N-bis(1-methylethyl)-3-[2-methyl-6-(3-methyl-5-isoxazolyl)pyrazolo[1,5-a]pyrimidin-7-yl].
CAS 1214496-02-2, Mar. 25, 2010, 1-Propanone, 345-methyl-1H-pyrazol-1-yl)-1-[3-[2-(trifluoromethyl)[1,2,4]triazolo[1,5-a]pyrimidin-7-yl]-1-piperidinyl].
CAS 1214486-88-0, Mar. 25, 2010, Methanone, (3,5-dimethyl-4-isoxazolyl)[3-[6-(methylsulfonyl)[1,2,4]triazolo[1,5-a]pyrimidin-7-yl]-1-piperidinyl].
CAS 1214449-93-0, Mar. 25, 2010, 1-Propanone, 3-(5-methyl-2-furanyl)-1-[3-(2-methylpyrazolo[1,5-a]pyrimidin-7-yl)-1-piperidinyl].
CAS 1214427-36-7, Mar. 25, 2010, Methanone, 5-isoxazolyl[3-[6-(methylsulfonyl)[1,2,4]triazolo[1,5-a]pyrimidin-7-yl]-1-piperidinyl].
CAS 1184920-74-8, Sep. 16, 2009, 1-Piperidinecarboxylic acid, 3-(6-cyano-2-methylpyrazolo[1,5-a]pyrimidin-7-yl)-, 1,1-dimethylethyl ester.
CAS 960201-98-3, Jan. 9, 2008, 1-Piperidinecarboxylic acid, 3-(2-methylpyrazolo[1,5-a]pyrimidin-7-yl)-,1,1-dimethylethyl ester.
CAS 960201-89-2, Jan. 9, 2008, 1-Piperidinecarboxylic acid, 3-[2-(1,1-dimethylethyl)pyrazolo[1,5-a]pyrimidin-7-yl]-, 1,1-dimethylethyl ester.
CAS 958718-11-1, Dec. 19, 2007, Ethanone, 2-(4-methoxyphenyl)-1-[3-[6-(methylsulfonyl)[1,2,4]triazolo[1,5-a]pyrimidin-7-yl]-1-piperidinyl].
CAS 958715-94-1, Dec. 19, 2007, 1-Piperidinecarboxylic acid, 3-[3-(4-methoxyphenyl)-2-methylpyrazolo[1,5-a]pyrimidin-7-yl]-,1,1-dimethylethyl ester.
CAS 958709-70-1, Dec. 19, 2007, Ethanone, 2-(4-fluorophenyl)-1-[3-[6-(methylsulfonyl)[1,2,4]triazolo[1,5-a]pyrimidin-7-yl]-1-piperidinyl].
CAS 958707-04-5, Dec. 19, 2007, Methanone, (3,5-difluorophenyl)[3-[6-(methylsulfonyl)[1,2,4]triazolo[1,5-a]pyrimidin-7-yl]-1-piperidinyl].
CAS 958706-09-7, Dec. 19, 2007, Methanone, [3-[6-(methylsulfonyl)[1,2,4]triazolo[1,5-a]pyrimidin-7-yl]-1-piperidinyl][4-(2-propen-1-yloxy)phenyl].

CAS 958706-04-2, Dec. 19, 2007, Methanone, cyclopentyl[3-[6-(methylsulfonyl)[1,2,4]triazolo[1,5-a]pyrimidin-7-yl]-1-piperidinyl].
CAS 958699-24-6, Dec. 19, 2007, Methanone, [3-(1,1-dimethylethyl)-1-methyl-1H-pyrazol-5-yl][3-[2-(trifluoromethyl)[1,2,4]triazolo[1,5-a]pyrimidin-7-yl]-1-piperidinyl].
CAS 958618-14-9, Dec. 18, 2007, Methanone, [3-[6-(methylsulfonyl)[1,2,4]triazolo[1,5-a]pyrimidin-7-yl]-1-piperidinyl](4,5,6,7-tetrahydrobenzo[b]thien-3-yl).
CAS 958615-91-3, Dec. 18, 2007, Ethanone, 2-(3-methoxyphenyl)-1-[3-[6-(methylsulfonyl)[1,2,4]triazolo[1,5-a]pyrimidin-7-yl]-1-piperidinyl].
CAS 958615-85-5, Dec. 18, 2007, Ethanone, 2-(2-methoxyphenyl)-1-[3-[6-(methylsulfonyl)[1,2,4]triazolo[1,5-a]pyrimidin-7-yl]-1-piperidinyl].
CAS 958606-22-9, Dec. 18, 2007, 1-Propanone, 1-[3-[6-(methylsulfonyl)[1,2,4]triazolo[1,5-a]pyrimidin-7-yl]-1-piperidinyl]-2-phenyl-.
CAS 958606-21-8, Dec. 18, 2007, 1-Butanone, 1-[3-[6-(methylsulfonyl)[1,2,4]triazolo[1,5-a]pyrimidin-7-yl]-1-piperidinyl]-2-phenyl-.
CAS 958606-01-4, Dec. 18, 2007, Methanone, 4-thiazolyl(3-[1,2,4]triazolo[1,5-a]pyrimidin-7-yl-1-piperidinyl).
CAS 958605-43-1, Dec. 18, 2007, 1-Piperidinecarboxylic acid, 3-[2-(3,4-dimethoxyphenyl)pyrazolo[1,5-a]pyrimidin-7-yl]-, 1,1-dimethylethyl ester.
CAS 958603-00-4, Dec. 18, 2007, 1-Propanone, 3-(2-furanyl)-1-[3-[6-(methylsulfonyl)[1,2,4]triazolo[1,5-a]pyrimidin-7-yl]-1-piperidinyl].
Cas 958596-76-4, Dec. 18, 2007, Methanone, (3-[1,2,4]triazolo[1,5-a]pyrimidin-7-yl-1-piperidinyl)(3,4,5-trimethoxyphenyl).
CAS 958596-27-5, Dec. 18, 2007, Methanone, [3-[6-(methylsulfonyl)[1,2,4]triazolo[1,5-a]pyrimidin-7-yl]-1-piperidinyl]-2-pyridinyl.
CAS 958587-78-5, Dec. 18, 2007, Methanone, [4-methoxy-3-(1H-pyrazol-1-ylmethyl)phenyl](3-[1,2,4]triazolo[1,5-a]pyrimidin-7-yl-1-piperidinyl).
CAS 958586-33-9, Dec. 18, 2007, Ethanone, 2-(3-fluorophenyl)-1-[3-[6-(methylsulfonyl)[1,2,4]triazolo[1,5-a]pyrimidin-7-yl]-1-piperidinyl].
CAS 958586-25-9, Dec. 18, 2007, Methanone, [3-[6-(methylsulfonyl)[1,2,4]triazolo[1,5-a]pyrimidin-7-yl]-1-piperidinyl]-3-pyridinyl-.
CAS 958585-88-1, Dec. 18, 2007, Methanone, [5-(1,1-dimethylethyl)-3-methyl-2-furanyl][3-[6-(methylsulfonyl)[1,2,4]triazolo[1,5-a]pyrimidin-7-yl]-1-piperidinyl].
CAS 958585-13-2, Dec. 18, 2007, Methanone, (3,4-dimethoxyphenyl)[3-(2-methylpyrazolo[1,5-a]pyrimidin-7-yl)-1-piperidinyl].
CAS 958583-88-5, Dec. 18, 2007, Ethanone, 2-cyclopentyl-1-[3-[6-(methylsulfonyl)[1,2,4]triazolo[1,5-a]pyrimidin-7-yl]-1-piperidinyl].
CAS 958583-87-4, Dec. 18, 2007, 1-Propanone, 1-[3-[6-(methylsulfonyl)[1,2,4]triazolo[1,5-a]pyrimidin-7-yl]-1-piperidinyl]-3-phenyl-.
Cas 958583-82-9, Dec. 18, 2007, Methanone, cyclohexyl[3-[6-(methylsulfonyl)[1,2,4]triazolo[1,5-a]pyrimidin-7-yl]-1-piperidinyl].
CAS 958583-78-3, Dec. 18, 2007, Methanone, (2-fluorophenyl)[3-[6-(methylsulfonyl)[1,2,4]triazolo[1,5-a]pyrimidin-7-yl]-1-piperidinyl].
CAS 958573-20-1, Dec. 18, 2007, 1-Piperidinecarboxylic acid, 3-[2-methyl-3-(2-thienyl)pyrazolo[1,5-a]pyrimidin-7-yl]-, 1,1-dimethylethyl ester.
CAS 878693-18-6, Mar. 31, 2006, 1-Piperidinecarboxylic acid, 3-[2-(4-methoxyphenyl)pyrazolo[1,5-a]pyrimidin-7-yl]-, 1,1-dimethylethyl ester.
Cheng Qiong, Studies on synthesis and bioactivity of novel triazolopyrimidine derivatives, Chinese Doctoral Dissertations Full-text Database, Engineering Science and Technology I, vol. 04, pp. B014-196, 2009 (see English Abstract).

(56) References Cited

OTHER PUBLICATIONS

Tu Wen-long, Studies on structure-activity relationship of phosphodiesterase 2 inhibitors, Chinese Master's Theses Full-text Database, Engineering Science and Technology I, vol. 8, pp. B016-19, 2014 (see English Abstract).

* cited by examiner

[1,2,4]TRIAZOLO[1,5-A]PYRIMIDIN-7-YL COMPOUND

CROSS REFERENCE TO RELATED APPLICATIONS

This application is the national stage of PCT Application No. PCT/EP2016/076420, filed Nov. 2, 2016, which claims priority from European Patent Application No. 15192661.5, filed Nov. 2, 2015 and European Patent Application No. 15192966.8, filed Nov. 4, 2015 the entire disclosures of which are hereby incorporated in their entirety.

FIELD OF THE INVENTION

The present invention relates to a novel [1,2,4]triazolo[1,5-a]pyrimidin-yl derivative as inhibitor of phosphodiesterase 2 (PDE2). The invention is also directed to pharmaceutical compositions comprising the compound, to processes for preparing such compound and compositions, and to the use of such compound and compositions for the prevention and treatment of disorders in which PDE2 is involved, such as neurological and psychiatric disorders.

BACKGROUND OF THE INVENTION

Phosphodiesterases (PDEs) are a family of enzymes encoded by 21 genes and subdivided into 11 distinct families according to structural and functional properties. These enzymes metabolically inactivate widely occurring intracellular second messengers, 3',5'-cyclic adenosine monophosphate (cAMP) and 3',5'-cyclic guanosine monophosphate (cGMP). These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by PDEs. PDEs are hydrolases that inactivate cAMP and cGMP by catalytic hydrolysis of the 3'-ester bond, forming the inactive 5'-monophosphate (Scheme A).

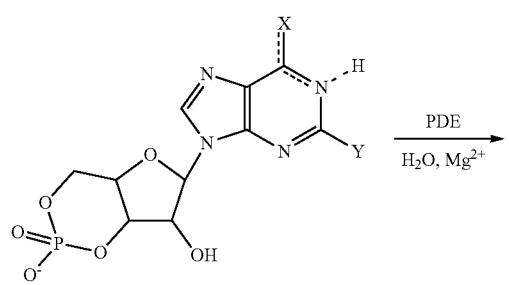

Scheme A cAMP X = NH$_2$, Y = H
cGMP X = O, Y = NH$_2$

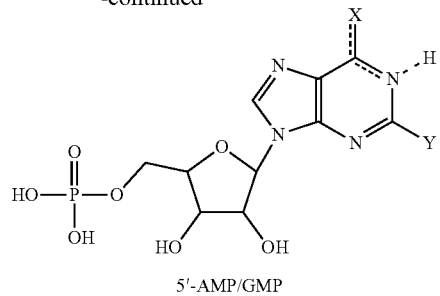

5'-AMP/GMP

On the basis of substrate specificity, the PDE families can be divided into three groups: i) the cAMP-specific PDEs, which include PDE4, 7 and 8; ii) the cGMP-selective enzymes PDE5, 6 and 9; and iii) the dual-substrate PDEs, PDE1, 2 and 3, as well as PDE10 and 11.

Furthermore, PDEs are expressed differentially throughout the organism, including the central nervous system. Different PDE isozymes therefore may have different physiological functions. Compounds that inhibit selectively PDE families or isozymes may display particular therapeutic activity, fewer side effects, or both.

Phosphodiesterase 2A (PDE2A) inactivates intracellular signalling mechanisms reliant on cyclic nucleotide signalling mediated by cAMP and cGMP via their degradation (by hydrolyzing the biologically relevant second messengers cAMP and cGMP into nonsignalling AMP and GMP, respectively). Such signalling pathways are known to play a role in the regulation of genes involved in the induction of synaptic plasticity.

The pharmacological inhibition of PDE2 therefore causes increased levels of synaptic plasticity (an underlying correlate of learning and memory), suggesting that PDE2A modulation may be a target for alleviating cognitive deficits seen in people suffering from disorders such as for example, schizophrenia, Alzheimer's disease, Parkinson's disease and other CNS disorders associated with cognitive dysfunction.

Phosphodiesterase 2A (PDE2A) is more abundantly expressed in the brain relative to peripheral tissues. The high expression of PDE2 in the limbic system (isocortex, hippocampus, amygdala, habenula, basal ganglia) suggests that PDE2 may modulate neuronal signalling involved in emotion, perception, concentration, learning and memory. Additionally, PDE2 is expressed in the nucleus accumbens, the olfactory bulb, the olfactory tubercle and the amygdala, supporting the suggestion that PDE2 may also be involved in anxiety and depression. (see for instance, Lakies, V. et al. (2010) Quantitative comparison of phosphodiesterase mRNA distribution in human brain and peripheral tissues. Neuropharmacol. 59, 367-374).

Additionally, PDE2 inhibitors have been shown to be beneficial in the reduction of oxidative stress-induced anxiety, supporting their use in the treatment of anxiety in neuropsychiatric and neurodegenerative disorders that involve oxidative stress, such as Alzheimer's disease, Parkinson's disease and multiple sclerosis.

PDE2 inhibitors have been shown to enhance long term potentiation of synaptic transmission and to improve memory acquisition and consolidation in the object recognition and in the social recognition tests in rats. Furthermore, PDE2 inhibitors have been shown to reverse the MK-801 induced working memory deficit in the T-maze in mice. PDE2 inhibitors have also been shown to display activity in forced swim test and light/dark box models; and to show anxiolytic-like effects in elevated plus-maze, hole-board and open-field tests and to prevent stress-induced changes in apoptosis and behaviour.

Thus, PDE2 inhibitors may be useful in the treatment of memory deficiency, cognitive disorders, anxiety, bipolar disorder and depression.

WO2015/164508 (Dart Neuroscience, LLC) discloses substituted [1,2,4]triazolo[1,5-a]pyrimidin-yl compounds as PDE2 inhibitors.

There is still a need for PDE2 inhibitor compounds with an advantageous balance of properties, such as for example selectivity for PDE2, good chemical stability and target engagement by occupying PDE2 and increasing cyclic nucleotides levels in relevant brain regions.

SUMMARY OF THE INVENTION

It is the object of the present invention to provide a novel inhibitor of PDE2 that may be potentially useful in the treatment of diseases related to PDE2 enzyme activity.

Thus, the present invention is directed to compound 1

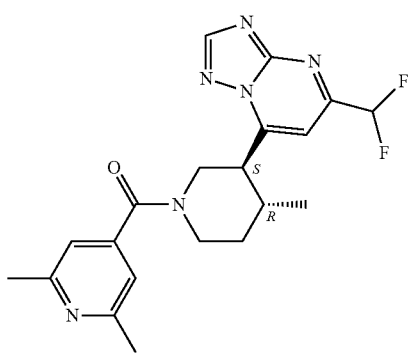

(1)

or a pharmaceutically acceptable salt or a solvate thereof.

In a particular embodiment, the pharmaceutically acceptable salt is a hydrochloride salt, more in particular, the 0.2HCl salt.

Illustrative of the invention is a pharmaceutical composition comprising a pharmaceutically acceptable carrier and compound 1 above, or a pharmaceutically acceptable salt or a solvate thereof. An illustration of the invention is a pharmaceutical composition made by mixing compound 1 above, or a pharmaceutically acceptable salt or a solvate thereof, and a pharmaceutically acceptable carrier. Illustrating the invention is a process for making a pharmaceutical composition comprising mixing compound 1 above, or a pharmaceutically acceptable salt or a solvate thereof, and a pharmaceutically acceptable carrier.

Further illustrative of the invention are methods to enhance neuronal plasticity comprising administering to a subject in need thereof a therapeutically effective amount of compound 1, or a pharmaceutically acceptable salt or a solvate thereof, or pharmaceutical compositions described above.

Exemplifying the invention are methods of treating a disorder mediated by the PDE2 enzyme, comprising administering to a subject in need thereof a therapeutically effective amount of compound 1, or a pharmaceutically acceptable salt or a solvate thereof, or pharmaceutical compositions described above.

Further exemplifying the invention are methods of inhibiting the PDE2 enzyme, comprising administering to a subject in need thereof a therapeutically effective amount of compound 1, or a pharmaceutically acceptable salt or a solvate thereof, or pharmaceutical compositions described above.

An example of the invention is a method of treating a disorder selected from the group consisting of neurological and psychiatric disorders, comprising administering to a subject in need thereof, a therapeutically effective amount of compound i, or a pharmaceutically acceptable salt or a solvate thereof, or pharmaceutical compositions described above.

An example of the invention is a method of treating a disorder selected from the group of neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; stroke; and autistic disorders, comprising administering to a subject in need thereof, a therapeutically effective amount of compound 1, or a pharmaceutically acceptable salt or a solvate thereof, or a pharmaceutically acceptable salt or a solvate thereof or pharmaceutical compositions described above.

An example of the invention is a method of treating a disorder selected from the group consisting of neurological and psychiatric disorders comprising administering to a subject in need thereof, a therapeutically effective amount of compound 1 or a pharmaceutically acceptable salt or a solvate thereof, or pharmaceutical compositions described above.

An example of the invention is a method of treating a disorder selected from the group of neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; stroke; and autistic disorders, comprising administering to a subject in need thereof, a therapeutically effective amount of compound 1 or a salt or a solvate thereof, or pharmaceutical compositions described above.

Also exemplifying the invention is compound i or a salt or a solvate thereof, or a pharmaceutical composition described above, for use as a medicament.

Further exemplifying the invention is compound 1 or a salt or a solvate thereof, or a pharmaceutical composition according to the invention for use in the treatment, prevention, amelioration, control or reduction of the risk of various neurological and psychiatric disorders associated with phosphodiesterase 2 dysfunction in a mammal, including a human, the treatment or prevention of which is affected or facilitated by the inhibition of phosphodiesterase 2.

An example of the invention is compound 1 or a pharmaceutically acceptable salt or a solvate thereof according to the present invention or a pharmaceutical composition according to the invention for use in the treatment, prevention, amelioration, control or reduction of the risk of various disorders selected from psychotic disorders and conditions; anxiety disorders; movement disorders; drug abuse; mood disorders; neurodegenerative disorders; disorders or conditions comprising as a symptom a deficiency in attention and/or cognition; stroke; and autistic disorder.

An example of the invention is a method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of compound 1 or a pharmaceutically acceptable salt of a solvate thereof, or pharmaceutical compositions described above.

Another example of the invention is compound 1 or a pharmaceutically acceptable salt or a solvate thereof described above for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease, (i) dementia associated with beta-amyloid, (j) depressive disorders and (k) anxiety disorders, in a subject in need thereof.

DESCRIPTION OF THE FIGURES

FIGS. 5a and 5b show the effect of compound 1 on weak HFS-induction of long term potentiation (LTP) at the mossy fiber synapse.

DETAILED DESCRIPTION OF THE INVENTION

Definitions

Figure 1A:
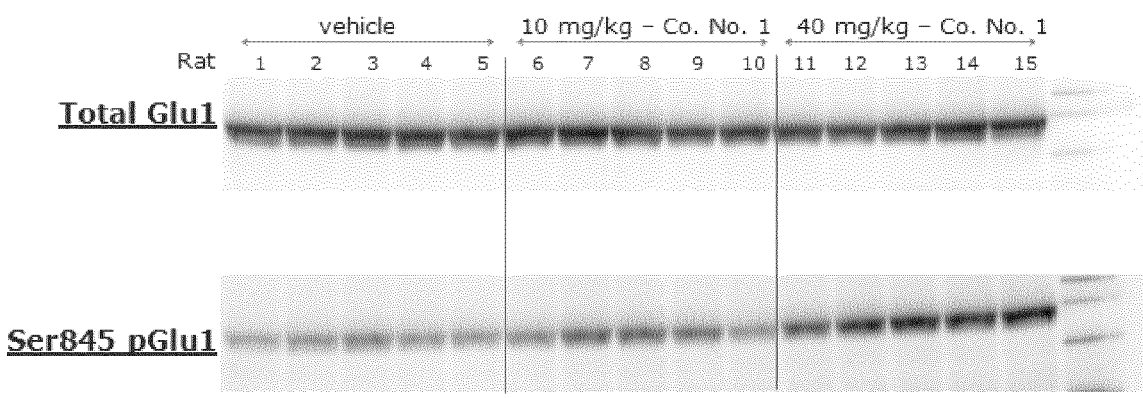
FIG. 1 shows the effect of compound 1 on pGlu1 levels in the hippocampus of Sprague Dawley rats (10 mg/kg and 40 mg/kg Compound 1). Western blots from individual rats are shown (n=5 per treatment) (FIG. 1a). Quantification (pGlu normalized against total Glu1 levels) is shown in FIG. 1b.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The term "host" refers to a mammal, in particular to humans, mice, dogs and rats.

The term "cell" refers to a cell expressing or incorporating the PDE2 enzyme.

The term "compound of the invention" as used herein, is meant to include compound 1, and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

The absolute configuration is specified according to the Cahn-Ingold-Prelog system. The configuration at an asymmetric atom is specified by either R or S.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers.

In addition, the compound of the present invention may form solvates with water (i.e., hydrates) or common organic solvents, and such solvates are also intended to be encompassed within the scope of this invention.

For use in medicine, the salts of compound 1 refer to non-toxic "pharmaceutically acceptable salts". Other salts may, however, be useful in the preparation of compound 1 or of its pharmaceutically acceptable salts. Suitable pharmaceutically acceptable salts of compound 1 include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-othanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid.

Pharmacology

The compound according to the invention inhibits PDE2 enzyme activity, in particular PDE2A, and hence raises the levels of cAMP or cGMP within cells that express PDE2. Accordingly, inhibition of PDE2 enzyme activity may be useful in the treatment of diseases caused by deficient amounts of cAMP or cGMP in cells. PDE2 inhibitors may also be of benefit in cases in which raising the amount of cAMP or cGMP above normal levels results in a therapeutic effect. Inhibitors of PDE2 may be used to treat neurological and psychiatric disorders.

Hence, the present invention relates to compound 1 or a pharmaceutically acceptable salt or a solvate thereof according to the present invention, for use as a medicine, as well as to the use of compound 1 or a pharmaceutically acceptable salt or a solvate thereof according to the invention or a pharmaceutical composition according to the invention for the manufacture of a medicament. The present invention also relates to compound 1 or a pharmaceutically acceptable salt or a solvate thereof according to the present invention or a pharmaceutical composition according to the invention for use in the treatment or prevention of, in particular treatment of, a condition in a mammal, including a human, the treatment or prevention of which is affected or facilitated by the inhibition of phosphodiesterase 2 enzyme. The present invention also relates to the use of compound 1 or a pharmaceutically acceptable salt or a solvate thereof according to the present invention or a pharmaceutical composition according to the invention for the manufacture of a medicament for the treatment or prevention of, in particular treatment of, a condition in a mammal, including a human, the treatment or prevention of which is affected or facilitated by the inhibition of phosphodiesterase 2 enzyme.

The present invention also relates to compound 1 or a pharmaceutically acceptable salt or a solvate thereof according to the invention, or a pharmaceutical composition according to the invention for use in the treatment, prevention, amelioration, control or reduction of the risk of various neurological and psychiatric disorders associated with phosphodiesterase 2 dysfunction in a mammal, including a human, the treatment or prevention of which is affected or facilitated by the inhibition of phosphodiesterase 2.

Also, the present invention relates to the use of compound 1 or a pharmaceutically acceptable salt or a solvate thereof according to the invention or a pharmaceutical composition according to the invention for the manufacture of a medicament for treating, preventing, ameliorating, controlling or reducing the risk of various neurological and psychiatric disorders associated with phosphodiesterase 2 dysfunction in a mammal, including a human, the treatment or prevention of which is affected or facilitated by the inhibition of phosphodiesterase 2.

Where the invention is said to relate to the use of compound 1 or a pharmaceutically acceptable salt or a solvate thereof or composition according to the invention for the manufacture of a medicament for e.g. the treatment of a subject, e.g. a mammal, it is understood that such use is to be interpreted in certain jurisdictions as a method of e.g. treatment of a subject, comprising administering to a subject in need of such e.g. treatment, an effective amount of compound 1 or a pharmaceutically acceptable salt or a solvate thereof or composition according to the invention.

In particular, the indications that may be treated with PDE2 inhibitors, either alone or in combination with other drugs, include, but are not limited to, those diseases thought to be mediated in part by the basal ganglia, prefrontal cortex and hippocampus.

These indications include neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; stroke; and autistic disorder or autism.

In particular, the psychotic disorders and conditions associated with PDE2 dysfunction include one or more of the following conditions or diseases: schizophrenia, for example of the paranoid, disorganized, catatonic, undifferentiated or residual type; schizophreniform disorder; schizoaffective disorder, such as delusional or depressive type; delusional disorder; substance-induced psychotic disorder such as psychosis induced by alcohol, amphetamine, cannabis, cocaine, hallucinogens, inhalants, opioids, or phencyclidine; personality disorders of the paranoid type; and personality disorder of the schizoid type.

In particular, the anxiety disorders include panic disorder; agoraphobia; specific phobia; social phobia; obsessive-compulsive disorder; post-traumatic stress disorder; acute stress disorder; and generalized anxiety disorder.

In particular, movement disorders include Huntington's disease and dyskinesia; Parkinson's disease; restless leg syndrome and essential tremor. Additionally, Tourette's syndrome and other tic disorders can be included.

In particular, the central nervous system disorder is a substance-related disorder selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal.

In particular, mood disorders and mood episodes include depression, mania and bipolar disorders. Preferably, the mood disorder is selected from the group of bipolar disorders (I and II); cyclothymic disorder; depression; dysthymic disorder; major depressive disorder; treatment-resistant depression; and substance-induced mood disorder.

In particular, neurodegenerative disorders include Parkinson's disease; Huntington's disease; dementia such as for example Alzheimer's disease; multi-infarct dementia; AIDS-related dementia or fronto temporal dementia. The neurodegenerative disorder or condition comprises dysfunction of striatal medium spiny neurons responses.

In particular, disorders or conditions comprising as a symptom a deficiency in attention and/or cognition include dementia, such as Alzheimer's disease; multi-infarct dementia; dementia due to Lewy body disease; alcoholic dementia or substance-induced persisting dementia; dementia associated with intracranial tumours or cerebral trauma; dementia associated with Huntington's disease; dementia associated with Parkinson's disease; AIDS-related dementia; dementia due to Pick's disease; dementia due to Creutzfeldt-Jakob disease; other diseases include delirium; amnestic disorder; post-traumatic stress disorder; stroke; progressive supranuclear palsy; mental retardation; a learning disorder; attention-deficit/hyperactivity disorder (ADHD); mild cognitive disorder, Asperger's syndrome; age-related cognitive impairment; and cognitive impairment related to perception, concentration, learning or memory.

In particular, disorders related to memory acquisition and consolidation include, memory disorders, such as age-associated memory losses, memory deficiency.

Preferably, the psychotic disorder is selected from the group of schizophrenia, delusional disorder, schizoaffective disorder, schizophreniform disorder and substance-induced psychotic disorder.

Preferably, the central nervous system disorder is a personality disorder selected from the group of obsessive-compulsive personality disorder and schizoid, schizotypal disorder.

Preferably, the central nervous system disorder is a mood disorder selected from the group of bipolar disorders (I & II), cyclothymic disorder, depression, dysthymic disorder, major depressive disorder; treatment-resistant depression; and substance-induced mood disorder.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Preferably the disorders treated by compounds 1 or a pharmaceutically acceptable salt or a solvate thereof of the present invention are selected from schizophrenia; obsessive-compulsive disorder; generalized anxiety disorder; Huntington's disease; dyskinesia; Parkinson's disease; depression; bipolar disorders; dementia such as Alzheimer's disease; attention-deficit/hyperactivity disorder; drug abuse; stroke; and autism.

Preferably, the disorders treated by compounds 1 or a pharmaceutically acceptable salt or a solvate thereof of the present invention are schizophrenia, including positive and negative symptoms thereof, and cognitive deficits, such as impaired attention or memory.

Of the disorders mentioned above, the treatment of anxiety, obsessive-compulsive disorder, post-traumatic stress disorder; generalized anxiety disorder, schizophrenia, depression, attention-deficit/hyperactivity disorder, Alzheimer's disease, dementia due to Huntington's disease, dementia due to Parkinson's disease, dementia of the Alzheimer's type, substance-induced persisting dementia and mild cognitive impairment are of particular importance.

Of the disorders mentioned above, the treatment of anxiety, obsessive-compulsive disorder, schizophrenia, depression, attention-deficit/hyperactivity disorder, and Alzheimer's disease are of particular importance.

Other central nervous system disorders include schizoanxiety disorder, and comorbid depression and anxiety, in particular major depressive disorder with comorbid generalized anxiety disorder, social anxiety disorder, or panic disorder; it is understood that comorbid depression and anxiety may also be referred to by the terms anxious depression, mixed anxiety depression, mixed anxiety-depressive disorder, or major depressive disorder with anxiety symptoms, which are used indistinctively herein.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses. For example, the "American Psychiatric Association: Diagnostic and Statistical Manual of Mental Disorders, Fifth Edition. Arlington, Va., American Psychiatric Association, 2013" (DSM-5™) utilizes terms such as depressive disorders, in particular, major depressive disorder, persistent depressive disorder (dysthymia), substance-medication-induced depressive disorder; neurocognitive disorders (NCDs) (both major and mild), in particular, neurocognitive disorders due to Alzheimer's disease, vascular NCD (such as vascular NCD present with multiple infarctions), NCD due to HIV infection, NCD due to traumatic brain injury (TBI), NCD due to Parkinson's disease, NCD due to Huntington's disease, frontotemporal NCD, NCD due to prion disease, and substance/medication-induced NCD; neurodevelopmental disorders, in particular, intellectual disability, specific learning disorder, neurodevelopmental motor disorder, communication disorder, and attention-deficit/hyperactivity disorder (ADHD); substance-related disorders and addictive disorders, in particular, alcohol use disorder, amphetamine use disorder, cannabis use disorder, cocaine use disorder, other hallucinogen use disorder, tobacco use disorder, opiod use disorder, and phencyclidine use disorder; schizophrenia spectrum and other psychotic disorders, in particular, schizophrenia, schizophreniform disorder, schizoaffective disorder, delusional disorder, brief psychotic disorder, substance/medication-induced psychotic disorder; and cyclothymic disorder (which under DSM-5™ falls under the bipolar and related disorders category). Such terms may be used by the skilled person as an alternative nomenclature for some of the diseases or conditions referred to herein. An additional neurodevelopmental disorder includes autism spectrum disorder (ASD), which encompasses according to the DSM-5™, disorders previously known by the terms early infantile autism, childhood autism, Kanner's autism, high-functioning autism, atypical autism, pervasive developmental disorder not otherwise specified, childhood disintegrative disorder, and Asperger's disorder.

Therefore, the invention also relates to compound 1 or a pharmaceutically acceptable salt or a solvate thereof according to the invention, for use in the treatment of any one of the diseases mentioned hereinbefore.

The invention also relates to compound 1 or a pharmaceutically acceptable salt or a solvate thereof according to the invention for use in treating any one of the diseases mentioned hereinbefore.

The invention also relates to compound 1 or a pharmaceutically acceptable salt or a solvate thereof according to the invention, for the treatment or prevention, in particular treatment, of any one of the diseases mentioned hereinbefore.

The invention also relates to the use of compound 1 or a pharmaceutically acceptable salt or a solvate thereof according to the invention, for the manufacture of a medicament for the treatment or prevention of any one of the disease conditions mentioned hereinbefore.

The invention also relates to the use of compound 1 or a pharmaceutically acceptable salt or a solvate thereof according to the invention for the manufacture of a medicament for the treatment of any one of the disease conditions mentioned hereinbefore.

Compound 1 or a pharmaceutically acceptable salt or a solvate thereof of the present invention can be administered to mammals, preferably humans, for the treatment or prevention of any one of the diseases mentioned hereinbefore.

In view of the utility of compound 1, or a pharmaceutically acceptable salt or a solvate thereof, according to the invention, there is provided a method of treating a disorder or disease mentioned hereinbefore, comprising administering to a subject in need thereof, a therapeutically effective amount of compound 1 or a pharmaceutically acceptable salt or a solvate thereof or pharmaceutical compositions described herein.

Said methods comprise the administration, i.e. the systemic or topical administration, preferably oral administration, of a therapeutically effective amount of compound 1 or a pharmaceutically acceptable salt or a solvate thereof according to the invention to warm-blooded animals, including humans.

Therefore, the invention also relates to a method for the prevention and/or treatment of any one of the diseases mentioned hereinbefore comprising administering a therapeutically effective amount of compound 1 or a pharmaceutically acceptable salt or a solvate thereof according to the invention to a patient in need thereof.

The PDE2 inhibitor described herein can be used alone, in combination or in combination with other pharmaceutical agents such as other agents used in the treatment of psychoses, such as schizophrenia and bipolar disorder, obsessive-compulsive disorder, Parkinson's disease, cognitive impairment and/or memory loss, e.g. nicotinic α-7 agonists, PDE4 inhibitors (Rolipram, GEBR-7b, GSK356278, GSK256066, Apremilast, MK-0952, Roflumilast, AN2898, AN2728, Ariflo Cilomilast, Dotraverine, Ronomilast Elbimilast, Revamilast, Tetomilast, E6005, GDP-1116, HT0712, MK-0873), PDE5 inhibitors (Sildenafil, Vardenafil, Tadalafil, Udenafil, Avanafil, Mirodenafil, Lodenafil, Dasantafil, PF-00489791), PDE9 (PF-04447943), other PDE2 inhibitors (Bay 60-7550, PF-999, ND-7001), PDE10 inhibitors (PF-02545920, AMGS79), PDE2 and 10 inhibitors, calcium channel blockers, muscarinic m1 and m2 modulators, adenosine receptor modulators, ampakines, NMDA-R modulators, mGluR modulators, dopamine modulators, serotonin modulators, cannabinoid modulators, HDAC inhibitors (Vorinostat SAHA, Panobinostat, Quisinostat, Valproic acid) and cholinesterase inhibitors (e.g. donepezil, rivastigmine, and galantamine). In such combinations, the compound 1 or a pharmaceutically acceptable salt or a solvate thereof of the present invention may be utilized in combination with one or more other drugs in the treatment, prevention, control, amelioration, or reduction of risk of diseases or conditions for which compound 1 or the other drugs may have utility, where the combination of the drugs together are safer or more effective than either drug alone.

One skilled in the art will recognize that a therapeutically effective amount of the PDE2 inhibitor of the present invention is the amount sufficient to inhibit the PDE2 enzyme and that this amount varies inter alia, depending on the type of disease, the concentration of the compound in the therapeutic formulation, and the condition of the patient. Generally, an amount of PDE2 inhibitor to be administered as a therapeutic agent for treating diseases in which inhibition of the PDE2 enzyme is beneficial, such as the disorders described herein, will be determined on a case by case by an attending physician.

Generally, a suitable dose is one that results in a concentration of the PDE2 inhibitor at the treatment site in the range of 0.5 nM to 200 μM, and more usually 5 nM to 50 μM. To obtain these treatment concentrations, a patient in need of treatment likely will be administered between 0.001 mg/kg to 15 mg/kg body weight, in particular from 0.01 mg/kg to 2.50 mg/kg body weight, in particular, from 0.01 to 1.5 mg/kg body weight, in particular from 0.1 mg/kg to 0.50 mg/kg body weight. The amount of a compound according to the present invention, also referred to here as the active ingredient, which is required to achieve a therapeutical effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compound according to the invention is preferably formulated prior to admission. As described herein below, suitable pharmaceutical formulations are prepared by known procedures using well known and readily available ingredients.

Pharmaceutical Compositions

The present invention also provides compositions for preventing or treating diseases in which inhibition of PDE2 is beneficial, such as neurological and psychiatric disorders. Said compositions comprising a therapeutically effective amount of compound 1 and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compound can be used for systemic administration such as oral, percutaneous or parenteral administration; or topical administration such as via inhalation, a nose spray, eye drops or via a cream, gel, shampoo or the like. The compound is preferably orally administered.

The exact dosage and frequency of administration depends on the compound, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compound of the instant invention.

The amount of compound 1 that can be combined with a carrier material to produce a single dosage form will vary depending upon the disease treated, the mammalian species, and the particular mode of administration. However, as a general guide, suitable unit doses for the compound of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

For the compositions, methods and kits provided above, one of skill in the art will understand that the preferred compound for use in each is the compound noted herein Experimental Part As used herein, the term "ACN" means acetonitrile, "AcOH" means acetic acid, "DMAP" 4-dimethylaminopyridine, "DSC" means differential scanning calorimetry, "LCMS" means liquid chromatography/mass spectrometry, "HPLC" means high-performance liquid chromatography, "RP HPLC" means reverse phase high-performance liquid chromatography, "aq." means aqueous, "DCM" means dichloromethane, "DIPE" means diisopropyl ether, "DIPEA" means diisopropylethyl amine, "DMF" means N,N-dimethylformamide, "EtOH" means ethanol, "Et$_2$O" means diethylether, "EtOAc" means ethyl acetate, "Et$_3$N" means triethylamine, "HBTU" means O-(benzotriazol-1-yl)-N,N,N'N,'-tetramethyluroniumhexafluoro-phosphate, "THF" means tetrahydrofuran, "min" means minutes, "h" means hours, "MeOH" means methanol, "iPrOH" means 2-propanol, "RM" means reaction mixture, "RT" means room temperature, "OL" means organic layer, "R$_t$," means retention time (in minutes), "quant." means quantitative, "sat." means saturated, "sol." means solution, "m.p." means melting point, "q.s." means quantum sufficit.

Thin layer chromatography (TLC) was carried out on silica gel 60 F254 plates (Merck) using reagent grade solvents. Open column chromatography was performed on silica gel, mesh 230-400 particle size and 60 Å pore size (Merck) under standard techniques. Automated flash column chromatography was performed using ready-to-connect cartridges from Merck, on irregular silica gel, particle size 15-40 μm (normal phase disposable flash columns) on an SPOT or LAFLASH system from Armen Instrument.

The absolute stereochemical configuration for some of the compounds was determined using vibrational circular dichroism (VCD). They were measured on a Bruker Equinox 55 equipped with a PMA 37, in a KBr liquid cell using CD$_2$Cl$_2$ as solvent (PEM: 1350 cm-1, LIA: 1 mV, resolution: 4 cm$^{-1}$). A description on the use of VCD for the determination of absolute configuration can be found in Dyatkin A. B. et. al, Chirality, 14:215-219 (2002).

Ab initio calculations: A thorough conformational search is performed at molecular mechanics level using Macromodel to do a mixed torsional/low-mode sampling with the OPLS-2005 force field. The located minima were optimized using Jaguar on the B3LYP/6-31G level with a Poisson-Boltzmann continuum solvation model to mimic a dichloromethane solvent. All conformations within 10 kJ/mol interval were used to simulate VCD and IR spectrum. Dipole and rotational strengths were calculated at the same B3LYP/6-31G level, using Jaguar. The calculated VCD spectra, generated after scaling the frequencies with a factor of 0.97, converting to a Lorentzian bandshape, and summing up the contribution of each conformer assuming a Boltzmann ensemble, were visually compared with the experimental spectra for assigning the correct stereo chemistry.

The following examples are intended to illustrate but not to limit the scope of the present invention. Unless otherwise noted, all starting materials were obtained from commercial suppliers and used without further purification.

A. Synthesis of Intermediates

Intermediate 1

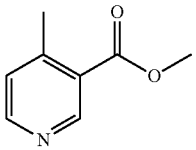

Procedure a: 4-Methyl-3-pyridinecarboxylic acid hydrochloride (1:1) (40 g, 230.4 mmol) was added to a refluxing mixture of sulphuric acid (20 mL) and MeOH (400 mL). The mixture was refluxed overnight, then it was evaporated and the resulting slurry was added to a cold solution of $NaHCO_3$ (64 g) in water (360 mL). The product was extracted with DCM and the organic layer was dried over $MgSO_4$, filtered and evaporated, yielding intermediate 1 (28.70 g, 83%).

Procedure b: A metal reactor was charged with 3-bromo-4-methyl-pyridine (200 g, 0.116 mol) and a mixture of DMF/MeOH (1 L/1 L). To this was added $Et_3N$ (400 g, 0.395 mol), palladium (II) acetate (8 g, 0.036 mol) and 1,1'-bis(diphenylphosphino)ferrocene (16 g, 0.029 mol). The reactor was closed and pressurized with CO gas (3 MPa) and the reaction mixture was stirred and heated overnight at 140° C. The RM was cooled, filtered and concentrated in vacuo. The residue was purified by flash column chromatography over silica gel (gradient eluent: EtOAc/Petroleum ether from 1/1 to 1/0). The product fractions were collected and the solvent was evaporated to afford the desired intermediate 1 (90 g, 51%).

Intermediate 2

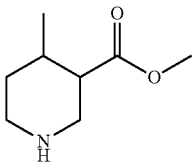

Procedure a: A hydrogenation flask was charged with AcOH (500 mL) and then $PtO_2$ (15.02 g, 66.2 mmol) was added. Intermediate 1 (50 g, 330.8 mmol) was added and the mixture was hydrogenated at 50° C. for 7 days. The RM was filtered over Dicalite® and the filtrate was evaporated to yield intermediate 2 (52 g), which was used in the next step without further purification.

Procedure b: Platinum oxide (5 g, 0.022-mol) was added to a solution of intermediate 1 (90 g, 0.595 mol) and AcOH (1 L). The r.m. was stirred and hydrogenated for 5 days at 50° C. under a pressure of 3.5 kPa. The cooled RM was concentrated in vacuo to give intermediate 2 as the acetic acid salt (140 g, 97%, 90% purity determined by $^1$H-NMR).

Intermediate 3

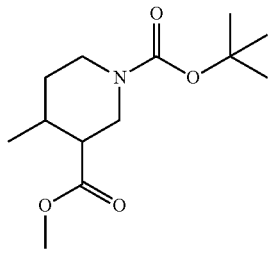

Procedure a: To a solution of intermediate 2 (52 g, 330.8 mmol) in DCM (869 mL), DIPEA (85.5 g, 661.5 mmol) and DMAP (4.04 g, 33.08 mmol) were added. Then di-tert-butyl dicarbonate (72.19 g, 330.8 mmol) was added to this solution in small portions and the reaction was stirred at RT for 1 h. The RM was washed with water and brine and the organic layer was dried over $MgSO_4$, filtered and evaporated. The product was purified by column chromatograph (silica gel, eluent: DCM, 1% MeOH in DCM, 2%, 4%). The desired fractions were evaporated, yielding intermediate 3 (64.1 g, 75%).

Procedure b: To a stirred and cooled (0° C.) solution of intermediate 2 (140 g, 0.595 mol) in DCM (1.5 L) was added sequentially di-tert-butyl dicarbonate (130 g, 0.596 mol), $Et_3N$ (225 g, 1.74 mol) and DMAP (10 g, 0.082 mol) and stirring was continued at RT for 2 h. The reaction mixture was poured onto $H_2O$ (500 mL) and extracted with DCM (2×100 mL). The organic layers were separated, dried ($Na_2SO_4$), and the solvent was evaporated to give crude intermediate 3 (150 g, 90%, 90% purity determined by $^1$H-NMR) which was used as such.

Intermediate 4

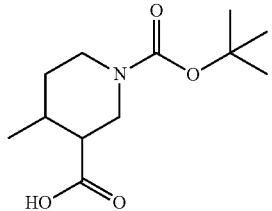

Procedure a: Intermediate 3 (64.1 g, 249.1 mmol) was stirred in MeOH (500 mL) at RT. NaOH (2 M, 747.3 mL) was added and the mixture was stirred for 2 h at RT. The RM was acidified with HCl 1N and the product was extracted with $Et_2O$. The OL was washed with brine and dried over $MgSO_4$, filtered and evaporated, yielding intermediate 4 (59.70 g) as a white solid.

Procedure b: To a stirred solution of intermediate 3 (150 g, 90% pure, 0.524 mol) in MeOH (0.9 L) was added a solution of a 2M NaOH solution (1.8 mol). After 14 h at RT, the RM was extracted with MTBE (2×0.8 L). The aqueous layer was acidified with 10% citric acid and then extracted with EtOAc (4×1 L). The combined organic layers were dried over $Na_2SO_4$, filtered and concentrated in vacuo to give crude intermediate 4 (142 g, 90% purity determined by $^1$H-NMR, 100%) which was used as such in the next step.

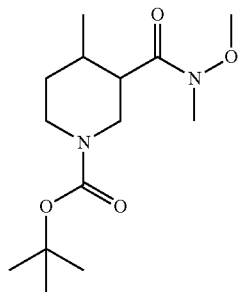

Intermediate 5

Procedure a: To a solution of intermediate 4 (59.7 g, 0.25 mol) in THF (800 mL), was added di-1H-imidazol-1-yl-methanone (54 g, 0.33 mol) and the mixture was stirred at RT for 1 h. In another flask, to a suspension of N-methoxy-methanamine hydrochloride (1:1) (32.93 g, 0.34 mol) in ACN (500 mL), was added trimethylamine (35.75 g, 0.35 mol). Both mixtures were combined and stirred at 50° C. while monitoring. The intermediate product crystallized out of the RM and did not react with N-methoxy-methanamine to form the desired product. DCM was added until the intermediate dissolved. The reaction was left stirring for 1 week at 80° C. The solvents were evaporated. The residue was dissolved in DCM and washed with water, 20% AcOH solution and finally with a saturated NaHCO$_3$ solution. The organic layer was dried over MgSO$_4$, filtered and evaporated. The product was purified by column chromatography (silica gel, eluent: 2% MeOH in DCM, 4%). The pure fractions were evaporated, yielding intermediate 5 (70 g, quantitative).

Procedure b: To a stirred and ice-cooled solution of intermediate 4 (140 g, 0.518 mol) in DCM (2 L) was added N,O-dimethylhydroxylamine (113 g, 1.16 mol) and Et$_3$N (113 g, 1.79 mol). Then HATU (235 g, 0.618 mol) was added and stirring was continued for 14 h. The solvent was evaporated and a NaHCO$_3$ solution (0.5 L) was added and then extracted with DCM (3×1 L). The combined organic layers were separated, dried over Na$_2$SO$_4$, filtered and concentrated in vacuo. The residue was purified by silica gel flash chromatography eluting with 1-10% EtOAc in petroleum ether to afford intermediate 5 (152 g, 100%).

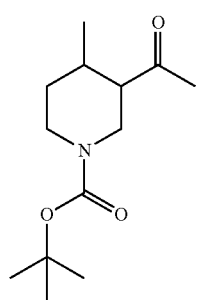

Intermediate 6

Procedure a: Intermediate 5 (70 g, 244.4 mmol) in THF (250 mL) was charged in a flask under N$_2$ and cooled to −15° C. Methylmagnesium bromide (1.4 M in toluene/THF 75/25, 206 mL) was added dropwise, with the temperature not exceeded 0° C. After addition, the RM was stirred at RT for 1 h. Then the RM was poured on ice with 20 mL AcOH. The product was extracted with Et$_2$O and the organic layer was washed with a 5% NaHCO$_3$ solution. The organic layer was dried over MgSO$_4$, filtered and evaporated to give intermediate 6 (53.35 g, 90%).

Procedure b: To a stirred and cooled solution (0° C.) of intermediate 5 (150 g, 0.524 mol) in TH (2 L) was added dropwise a 3M methylmagnesium bromide solution in THF (0.75 L, 2.25 mol) and stirring was continued at RT for 2 h. The reaction mixture was poured onto aqueous NH$_4$Cl solution and extracted with DCM. The combined organic layers were dried over Na$_2$SO$_4$, filtered and concentrated in vacuo. The residue was purified by silica gel chromatography eluting with 1-5% EtOAc in petroleum ether to afford intermediate 6 (120 g, 95%).

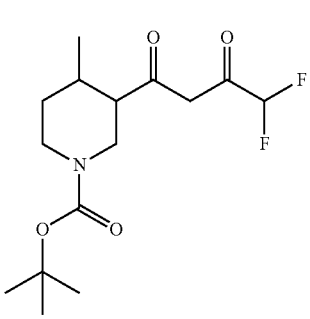

Intermediate 7

Intermediate 6 (53.35 g, 0.22 mol) was stirred in toluene (1500 mL) at 0° C. under N$_2$. Potassium tert-butoxide (34.14 g) was added at 0-5° C., 2,2-difluoro-acetic acid ethyl ester (33.01 g, 0.27 mol) was added dropwise at 0-5° C. The RM was stirred at RT for 2 h, then washed with 10% H$_2$SO$_4$ in water and the organic layer was dried on MgSO$_4$, filtered and evaporated, yielding intermediate 7 (70.50 g, quantitative).

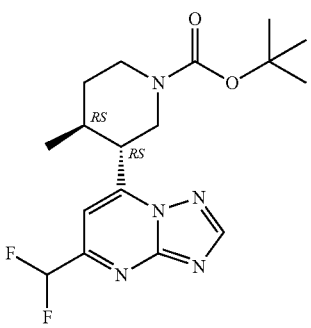

Intermediate 8

Intermediate 7 (70.5 g, 220.8 mmol), 1H-1,2,4-triazol-5-amine hydrochloride (1:1) (53.22 g, 441.52 mmol) and DMF (1500 mL) were stirred at 80° C. for 24 h. Et$_3$N (20 g) and di-tert-butyl dicarbonate (20 g) were added. The mixture was stirred for 30 min, evaporated and then dissolved in EtOAc, washed with water and brine. The organic layer was dried over MgSO$_4$, filtered and evaporated. Four isomers were observed. The first fraction crystallized from Et$_2$O. The crystals were filtered off and dried, yielding intermediate 8 (24.60 g, 30%). The mother liquor yielded a second fraction of the compound. The crystals were filtered off and dried, yielding intermediate 8 (2.53 g, 3%).

N.B. "RS" means the intermediate is a racemic mixture of two enantiomers of trans relative configuration.

Intermediate 9

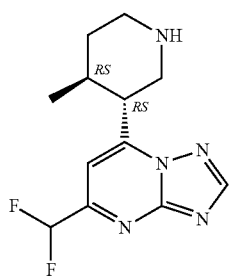

Intermediate 9a

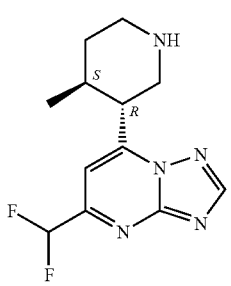

Intermediate 9b

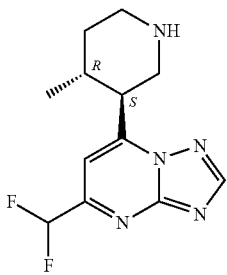

To a solution of intermediate 8 (24.6 g, 67 mmol) in MeOH (350 mL), was added HCl-iPrOH (350 mL) and the RM was stirred for 2 h at RT. The RM was evaporated and the product was crystallized from EtOH. The crystals were filtered off and dried, yielding 20.33 g of a crude, to which water, $Na_2CO_3$ and DCM were added. The organic layer was dried over $MgSO_4$, filtered and evaporated, yielding 12.80 g of intermediate 9. This free base was separated into enantiomers 9a and 9b by purification by Prep SFC (Stationary phase: Chiralpak Diacel AD 30×250 mm, mobile phase: $CO_2$, ((MeOH-iPrOH 50/50) with 0.4% $iPrNH_2$), yielding intermediate 9a (5 g, 19%, $R_t$=7.57 min) and intermediate 9b (5.13 g, 19%, $R_t$=9.36 min).

Intermediates 9a and 9b were isolated as free bases or alternatively, they were dissolved in MeOH, followed by addition of HCl/i-PrOH and the mixture evaporated. The hydrochloride salts (in each instance, .HCl) were crystallized from ACN, filtered off and dried.

B—Synthesis of Final Compound

Compound 1

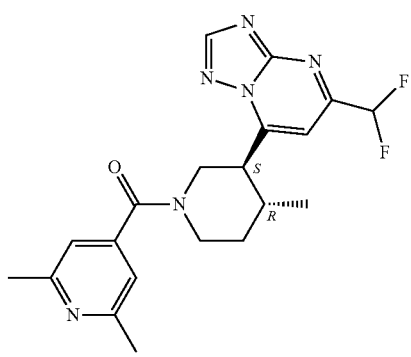

2,6-Dimethylpyridine-4-carboxylic acid (1.84 g, 12.2 mmol) was stirred in DCM (100 mL), DIPEA (6.31 g, 48.8 mmol) and HBTU (4.63 g, 12.2 mmol) were added, stirring was continued for 0.5 h at RT. Intermediate 9b (3.26 g, 12.2 mmol) was added to the solution and stirring was continued for 5 h at RT. NaOH 1N solution was added and stirred for 5 min. The organic layer was separated, dried over $MgSO_4$, filtered and evaporated. The product was purified by column chromatography (silica gel, eluent: 1% MeOH in DCM, 2%, 4%). The pure fractions were evaporated and the product was crystallized from DIPE, filtered off and dried, yielding compound 1 (3.85 g, 79%).

A separate batch of the compound was crystallized as HCl salt from $Et_2O$ to yield compound 1 as the hydrochloride salt (0.2 HCl) (yield: 175 mg, 70%, starting from 175 mg of intermediate 9b.HCl).

The stereoconfiguration of compound 1 was confirmed by vibrational circular dichroism (VCD).

Analytical Part

Melting Points

Values are either peak values or melt ranges, and are obtained with experimental uncertainties that are commonly associated with this analytical method.

DSC823e (indicated as DSC)

The melting point was determined with a DSC823e (Mettler-Toledo). The melting point was measured with a temperature gradient of 10° C./min. Maximum temperature was 300° C.

TABLE 1

| Co. No. | MP |
|---|---|
| 1 | 149.31 |

Optical Rotation

Optical rotation was measured on a Perkin-Elmer 341 polarimeter with a sodium lamp and reported as follows: [α]° (λ, c g/100 ml, solvent, T° C.).

$[α]_λ = (100α)/(l×c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 2

| Co. No. | OR |
|---|---|
| 1 | +28.91° (589 nm, c 0.2975 w/v %, DMF, 20° C.) |

SFC-MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE 3b

Analytical SFC data - $R_t$ means retention time (in minutes), $[M + H]^+$ means the protonated mass of the compound, method refers to the method used for (SFC)MS analysis of enantiomerically pure compounds.

| Co. No. | $R_t$ | $[M + H]^+$ | Method | Isomer Elution Order |
|---|---|---|---|---|
| 1 | 2.93 | 401 | 1 | Only one enantiomer |

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used. Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

TABLE 3a

Analytical SFC-MS Methods (Flow expressed in mL/min; column temperature (T) in ° C.; Run time in minutes, Backpressure (BPR) in bars.

| Method code | column | mobile phase | gradient | Flow Col T | Run time BPR |
|---|---|---|---|---|---|
| 1 | Daicel (AD, OD, OJ, AS, ID)-H-H column (5.0 μm, 250 × 4.6 mm) | A: $CO_2$ B: 5 different solvent for B used: MeOH, EtOH, iPrOH, MeOH—iPrOH (50-50) and EtOH—iPrOH (50-50) | 10%-55% B in 4 min, 55-50% in 0.45 min hold 2.55 min | 5 40 | 7 110 |

TABLE 4a

LCMS Method codes (Flow expressed in mL/min; column temperature (T) in °C.; Run time in minutes)

| Method code | Instrument | Column | Mobile phase | Gradient | Flow Col T | Run time (min) |
|---|---|---|---|---|---|---|
| Method A | Waters: Acquity ® UPLC ®- DAD-SQD | Waters: BEH C18 (1.7 µm, 2.1 * 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 mL/min 55° C. | 2 |

TABLE 4b

Analytical LCMS data - $R_t$ means retention time (in minutes), $[M + H]^+$ means the protonated mass of the compound, method refers to the method used for (LC)MS analysis.

| Co. No. | $R_t$ | $[M + H]^+$ | $[M + H]^+$ | Method |
|---|---|---|---|---|
| 1 | 0.76 | 401.2 | 399.2 | Method A |

Nuclear Magnetic Resonance (NMR)

The $^1$H NMR spectrum was recorded either on Bruker DPX-400 spectrometer with standard pulse sequences, operating at 400 MHz. Chemical shifts (δ) are reported in parts per million.

Co. No. 1: $^1$H NMR (400 MHz, DMSO-$d_6$, 120° C.) δ ppm 0.81 (d, J=6.6 Hz, 3H) 1.43 (qd, J=12.4, 4.4 Hz, 1H) 1.89 (br dq, J=13.4, 3.1 Hz, 1H) 2.44 (s, 6H) 2.49-2.53 (m, 1H) 3.11 (t, J=12.7 Hz, 1H) 3.35 (dd, J=12.9, 11.1 Hz, 1H) 3.57 (td, J=10.8, 4.1 Hz, 1H) 4.00-4.27 (m, 2H) 6.98 (t, J=54.2 Hz, 1H) 7.00 (s, 2H) 7.53 (s, 1H) 8.68 (s, 1H)

Pharmacological Examples

The compound provided in the present invention is an inhibitor of PDE2, particularly of PDE2A. The results of testing compound 1 in several pharmacological assays is shown below.

In Vitro Assay PDE2A

Human recombinant PDE2A (hPDE2A) was expressed in Sf9 cells using a recombinant rPDE10A baculovirus construct. Cells were harvested after 48 h of infection and the hPDE2A protein was purified by metal chelate chromatography on Ni-sepharose 6FF. Tested compounds were dissolved and diluted in 100% DMSO to a concentration 100 fold of the final concentration in the assay. Compound dilutions (0.4 µl) were added in 384 well plates to 20 µl of incubation buffer (50 mM Tris pH 7.8, 8.3 mM $MgCl_2$, 1.7 mM EGTA). 10l of hPDE2A enzyme in incubation buffer was added and the reaction was started by addition of 10 µl substrate to a final concentration of 10 µM cGMP and 0.01 µCi $^3$H-cGMP. The reaction was incubated for 45 minutes at room temperature. After incubation, the reaction was stopped with 20 µl of stop solution consisting of 17.8 mg/ml PDE SPA scintillation proximity assay) beads supplemented with 200 mM $ZnCl_2$. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value substracted with blanc value versus compound concentration and the half maximal inhibitory concentration ($IC_{50}$) value is derived from this curve.

In Vitro Assay PDE3A

Human recombinant PDE3A (hPDE3A) was supplied as a partially purified insect cell lysate by Scottish Biomedical, it was cloned from human brain and expressed in Sf9 cells. Tested compounds were dissolved and diluted in 100% DMSO to a concentration 100 fold of the final concentration in the assay. Compound dilutions (0.4 µl) were added in 384 well plates to 20 µl of incubation buffer (50 mM Tris pH 7.8, 8.3 mM $MgCl_2$, 1.7 mM EGTA). 10 µl of hPDE3A enzyme in incubation buffer was added and the reaction was started by addition of 10 µl substrate to a final concentration of 0.4 µM cAMP and 2.4 µCi/ml [$^3$H]-cAMP. The reaction was incubated for 60 min at room temperature. After incubation, the reaction was stopped with 20 µl of stop solution consisting of 17.8 mg/ml PDE SPA (scintillation proximity assay) beads supplemented with 200 mM $ZnCl_2$. After sedimentation of the beads during 30 min the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value substracted with blanc value versus compound concentration and the half maximal inhibitory concentration ($IC_{50}$) value is derived from this curve.

In Vitro Assay PDE10A

Rat recombinant PDE10A (rPDE10A2) was expressed in Sf9) cells using a recombinant rPDE10A baculovirus construct. Cells were harvested after 48 h of infection and the rPDE10A protein was purified by metal chelate chromatography on Ni-sepharose 6FF. Tested compounds were dissolved and diluted in 100% DMSO to a concentration 100 fold of the final concentration in the assay. Compound dilutions (0.4 µl) were added in 384 well plates to 20 µl of incubation buffer (50 mM Tris pH 7.8, 8.3 mM $MgCl_2$, 1.7 mM EGTA). 10 µl of rPDE10A enzyme in incubation buffer was added and the reaction was started by addition of 10 µl substrate to a final concentration of 60 nM cAMP and 0.008 µCi $^3$H-cAMP. The reaction was incubated for 60 minutes at room temperature. After incubation, the reaction was stopped with 20 µl of stop solution consisting of 17.8 mg/ml PDE SPA (scintillation proximity assay) beads. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value substracted with blanc value versus compound concentration and the half maximal inhibitory concentration ($IC_{50}$) value is derived from this curve.

TABLE 5a

| Compound | $IC_{50}$ PDE2A (nM) |
|---|---|
| 1 | 0.95 |
| 1.2HCl | 0.7 |

TABLE 5b $pIC_{50}$ corresponds to the −log IC50 expressed in mol/L.

| Compound | $pIC_{50}$ (PDE2A) | $pIC_{50}$ PDE3B | $pIC_{50}$ PDE10A2 |
|---|---|---|---|
| 1 | 9.07 | 5.21 | 7.06 |
| 1.2HCl | 9.11 | 5.15 | 6.93 |

Western Blot Detection of GLUR1 Phosphorylation

PDE2 is mainly expressed in hippocampus, cortex and striatum and can hydrolyze cAMP and cGMP. AMPA-R trafficking can be regulated through activation of PKA (via cAMP) or cGKII (via cGMP). Phosphorylation of the Glu1 subunit of the AMPA-R has been shown to be critical for LTD (decrease) and LTP (increase) expression and the retention of memories.

Methods

Compound 1 (solved in 10% CD+1 HCl) was administered p.o.(orally) to Sprague Dawley rats (180-200 g; 10 and 40 mg/kg) and 2 hours later, animals were sacrificed by decapitation. Hippocampus was dissected and tissue was snap frozen and stored at −80° C.

After thawing, tissue lysis was performed in Tissue Extraction Reagent supplemented with 5 mM EDTA and a protease and phosphatase inhibitor cocktail. Protein samples were denatured by LDS sample buffer and reducing agent (Life Technologies, Invitrogen, Carlsbad, Calif., USA) and finally, 50 μg of protein was loaded and electrophoresed using a 10% Bis-Tris polyacrylamide gel (Bio-Rad, Hercules, Calif., USA) at 90-160V. The proteins on the gels were then electroblotted onto a Trans blot turbo 0.2 μm nitrocellulose membrane (Bio-Rad), by using a Trans-blot Turbo transfer system (Bio-Rad). Membranes were blocked for 1 h at RT in Tween-20 Trisbuffered Saline (TBS-T: 10 mM Tris-HCl pH 8.0, 150 mM NaCl, 0.05% Tween-20) containing 5% non-fat dry milk (Santa Cruz Biotechnology, Dallas, Tex., USA), and incubated with the primary antibody overnight at 4° C. allowing gentle shaking (Total Glu1 Abcam 31232, Ser845 pGlu1 Abcam 76321, both dilution 1/1000). Blots were washed five times with TBS-T buffer and incubated with the secondary antibody for 1 h at RT (secondary donkey anti-rabbit HRP-conjugated, dilution 1/1000). Immunostaining was revealed after washing with TBST buffer via SuperSignal West Femto Maximum Sensitivity Substrate (Thermo scientific, Cramlington, United Kingdom). Signals were captured and quantified by chemiluminescence (G-box Syngene, Syngene, Cambridge, United Kingdom).

Figure 1B:
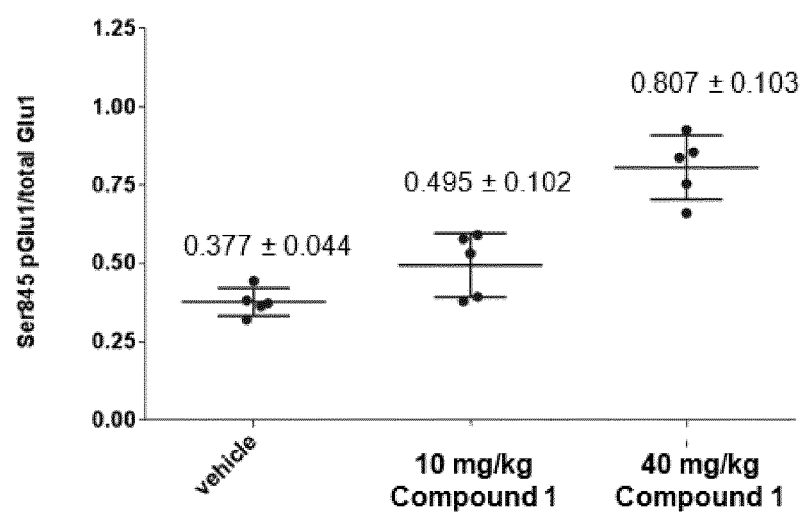

The results of this test are shown in FIG. 1.

PDE2 Occupancy by Compound 1

Methods

Occupancy of PDE2A was evaluated by ex-vivo autoradiography using [$^3$H]B-17a (described in WO02013/000924) as radioligand (compound 12 in Buijnsters et al., (2014). Structure-Based Design of a Potent, Selective, and Brain Penetrating PDE2 Inhibitor with Demonstrated Target Engagement. ACS Med Chem Lett. 5(9):1049-53.) Male Wistar rats (200-250 g) were treated by oral administration of vehicle or increasing doses of [$^3$H]B-17a and killed one hour after. Brains were immediately removed from the skull and rapidly frozen in dry-ice cooled 2-methylbutane (−40° C.). Twenty μm-thick striatal sections were cut using a Leica CM 3050 cryostat-microtome (van Hopplynus, Belgium), thaw-mounted on microscope slides (SuperFrost Plus Slides, LaboNord, France) and stored at −20° C. until use.

After thawing, sections were dried under a cold stream of air and incubated for one minute with 30 nM [$^3$H]B-17a in Tris-HCl (50 mM, pH7.4) containing 0.3% BSA. Brain sections from drug-treated and vehicle-treated animals were incubated in parallel. Non-specific binding was measured on cerebellar sections, a brain area which does not contain the PDE2A enzyme. After incubation, the excess of [$^3$H]B-17a was washed off in ice-cold buffer 2 times 10 minutes, followed by a quick dip in distilled water. The sections were then dried under a stream of cold air.

Brain sections were loaded in a β-imager (Biospace, Paris) for 4 hours and radioactivity emerging from delineated brain area was quantified using the Beta vision program (Biospace, Paris). Specific binding was determined as the difference between total binding in the striatum and non-specific binding in the cerebellum. Percentage receptor occupancy of the drug administered to the animal corresponded to 100% minus the percentage receptor labeled in the treated animal. For the determination of $ED_{50}$-values, the percentage of receptor occupancy was plotted against dose and the sigmoidal log dose-effect curve of best fit was calculated by non-linear regression analysis, using the GraphPad Prism program. $ED_{50}$s (the drug dose producing 50% receptor occupancy) with 95% confidence limits were calculated from the dose-response curves.

Figure 2:
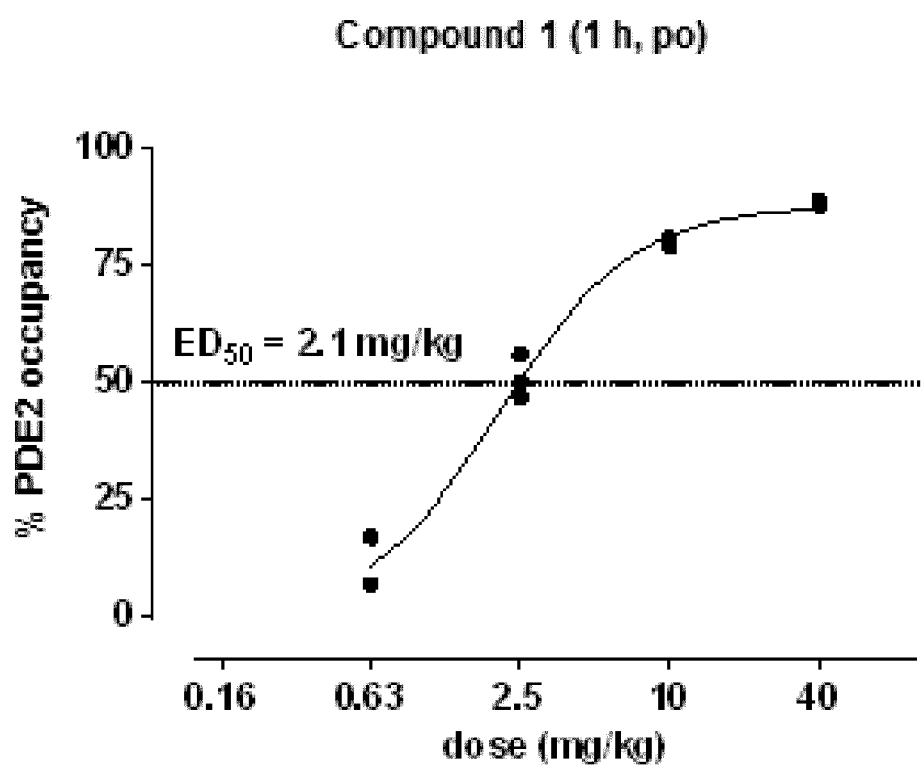
FIG. 2 shows occupancy of PDE2 by compound 1.

The results of this test are shown in FIG. 2.

Effect of Compound 1 on Synaptic Transmission

Critical Reagents

Sucrose dissection buffer contained (in mM) sucrose (150), NaCl (40), KCl (4), $NaH_2PO_4.H_2O$ (0.3), $MgCl_2.6H_2O$ (7), $NaHCO_3$(26), $CaCl_2.2H_2O$ (0.5), D-glucose (10), equilibrated with 95% $O_2$ and 5% $CO_2$ gas mixture. Artificial cerebrospinal fluid (ACSF) used during equilibration and recording contained (in mM): NaCl (124), KCl (2.7), $NaH_2PO_4.H_2O$ (1.25), $MgSO_4.7H_2O$ (1.3), $NaHCO_3$(26), $CaCl_2).2H_2O$ (2), D-glucose (10), Ascorbic acid (2), equilibrated with 95% $O_2$ and 5% $CO_2$ gas mixture. CNQX and Kynurenic acid were prepared in ACSF at a 50 μM and 1 mM concentration respectively. Compound 1 was prepared fresh from stock solution (with DMSO) in ACSF and with a final DMSO concentration that did not exceed 0.1%. All reagents were from Sigma-Aldrich, unless otherwise indicated.

Animals (Species, Weight, and Gender)

Animals used were male Sprague-Dawley rats with a weight range between 145 and 200 g provided by Charles River Germany.

Preparation of Hippocampal Slices

Horizontal brain slices (300 µm) were obtained from the mid- to ventral hippocampus of male Sprague-Dawley rats anesthetized with isofluorane according to standard protocol. Slices were cut using a vibrating tissue slicer (Leica VTI200S) in cold (4° C.) sucrose dissection buffer at a speed of 0.1 mm/s. After cut, slices were placed for equilibration at 35° C. for 20 min and then allowed to recover at RT for at least one hour in artificial cerebrospinal fluid (ACSF). Three to four slices were prepared from one brain.

Test System

All data were recorded with a MEA set-up commercially available from MultiChannel Systems MCS GmbH (Reutlingen, Germany) composed of a 4-channel stimulus generator and a 60-channels amplifier head-stage connected to a 60-channels A/D card. Software for stimulation, recordings and analysis are the ones commercially available from Multi Channel Systems: MC Stim (II 2.0.0 release) and MC Rack (3.8.1.0 release), respectively. All of the experiments were carried out with 3-dimensional MEA (Ayanda Biosystems, S.A., CH-1015 Lausanne, Switzerland) that consist of 60 tip-shaped and 60-µm-high electrodes spaced by 100 µm. The MEA electrodes are made of platinum with 600 kΩ<impedance<900 kΩ.

Experimental Design

The effect of compound 1 on synaptic transmission was investigated by recording the extracellular field potentials in hippocampal slices. It is well established that synaptic transmission a can generate a deflection of the extracellular field potential that reflects the synchronized synaptic activity in the population of neurons surrounding the recording electrode.

Extracellular field potential recordings. After recovery, brain slices were mounted on MEA chip under microscope and locating the 60 recording electrodes on the mossy fiber synapse (Dentate Gyrus-CA3) region of the hippocampus. ACSF solutions were continuously perfused at a rate of 2 mL/min. The temperature of the MEA chamber was maintained at 32±0.1° C. with a Peltier element located in the MBA amplifier headstage. All data were recorded with a MEA set-up commercially available from MultiChannel Systems MCS GmbH (Reutlingen, Germany). Two adjacent electrodes of the chip were selected to stimulate the mossy fibres in the hilar region of the dentate gyrus and the fEPSP was recorded the terminal zone area of the CA3 region of the hippocampus. Field extracellular post-synaptic potentials (fEPSPs) were evoked by stimulation of the mossy fibre input with two consecutive electrical pulses separated by 30 ms and repeated every 60 s (pulse width 100 µs, and current stimulation strength (µA) 40% relative maximum amplitude). Control experiments were performed simultaneously from slices that were randomly assigned to be treated with vehicle (DMSO). N represents the number of slices and usually 3-4 slices were used per animal. Evoked-responses at post-synaptic neurons level (fEPSP) are recorded if they satisfy certain quality criteria including: correct location, stable baseline (fluctuation within +/−10% during ten consecutive minutes, amplitude>100 µV. The fEPSP from selected electrodes were sampled at 5 kHz and recorded on the hard disk of a PC for offline analysis. In parallel, fEPSP amplitudes of selected electrodes were compiled online (with MC Rack program) to monitor and to follow the quality of the experiment. Data are plotted in a spreadsheet file for off-line analysis.

Weak Long Term Potentiation (LTP) was evoked by a single high frequency stimulus (HFS) to produce a less than maximal potentiation of the fEPSP.

Figure 3:
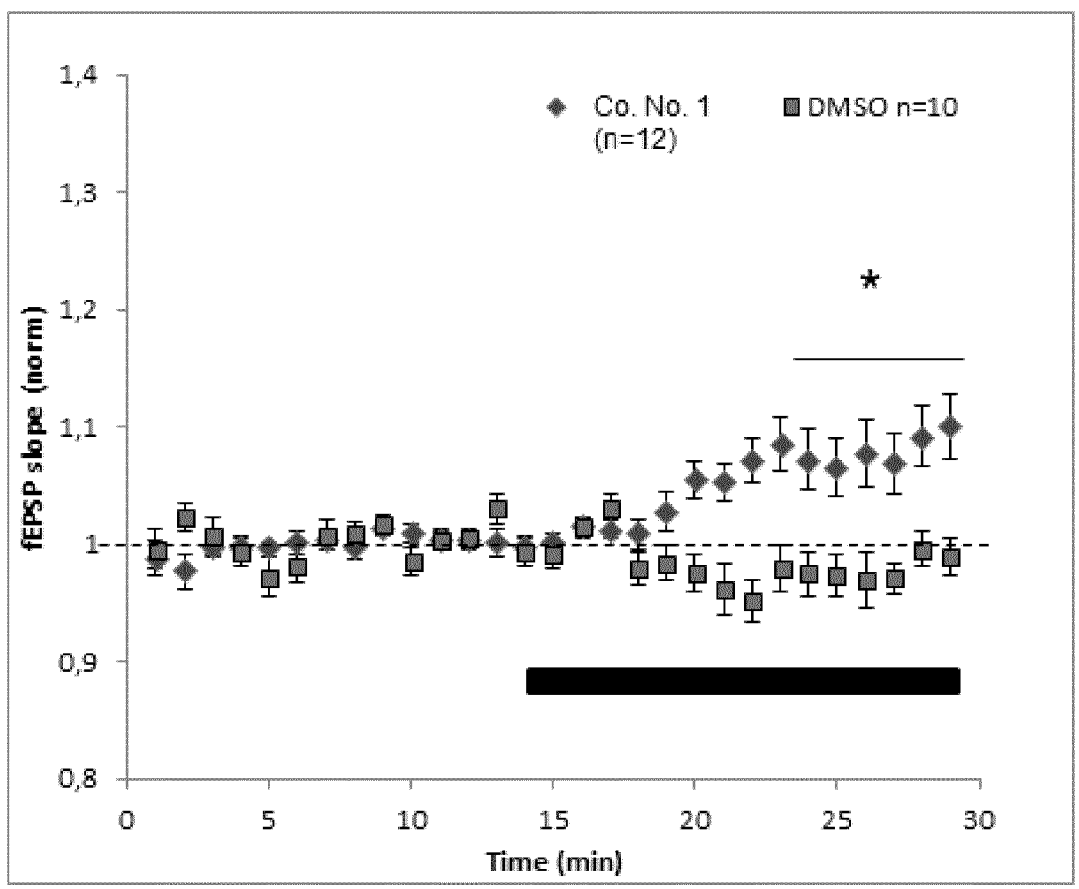
FIG. 3 shows the effect of compound 1 on basal synaptic transmission at the mossy fiber synapse.
Figure 4:
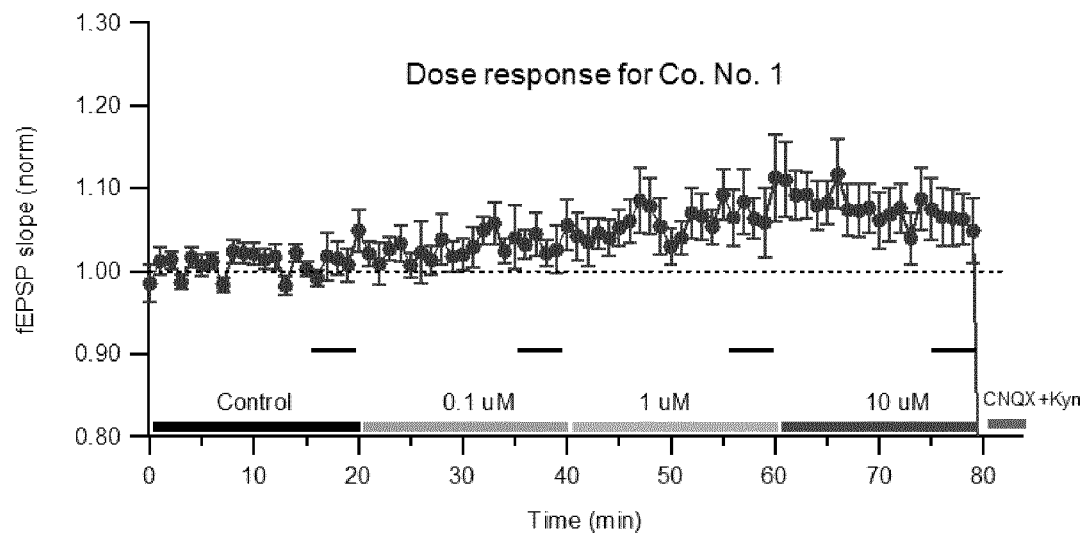
FIG. 4 shows the dose response effect of compound 1 on basal synaptic transmission at the mossy fiber synapse.
Figure 4:
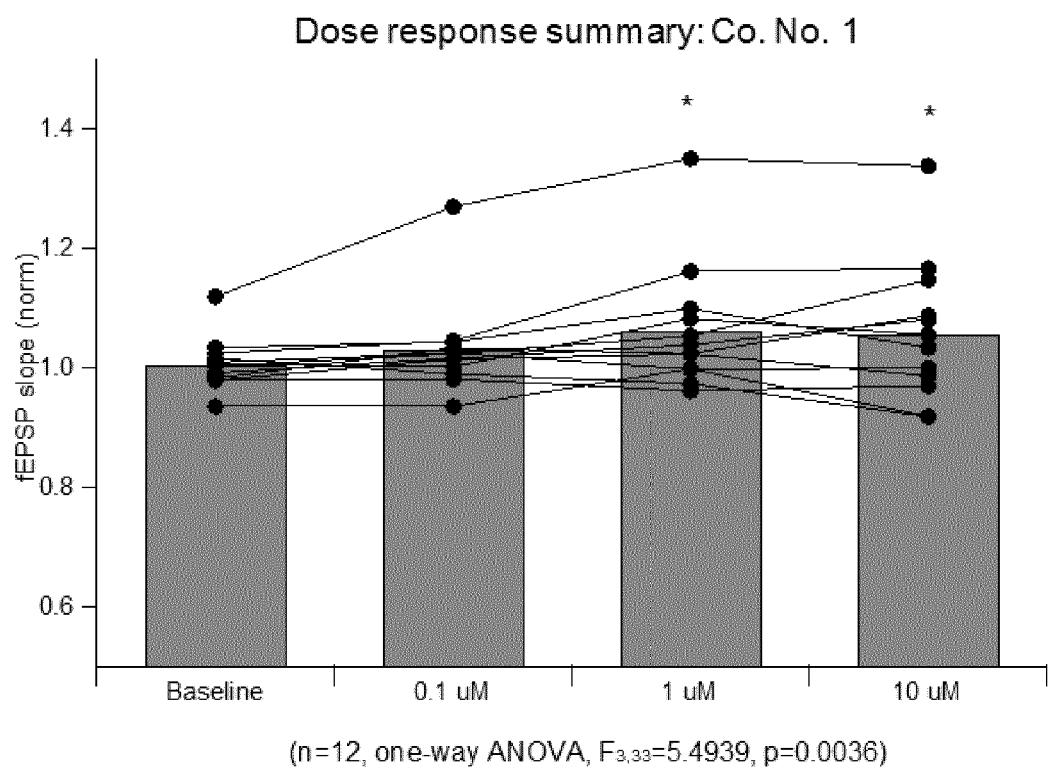
Figure 5A:
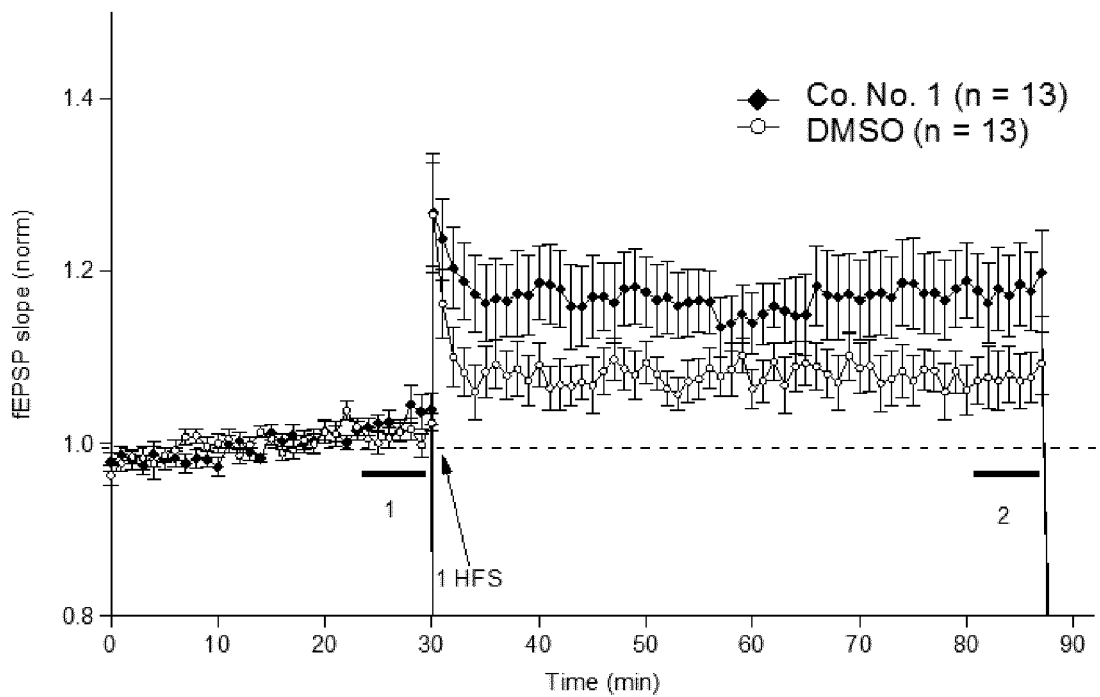
Figure 5A:
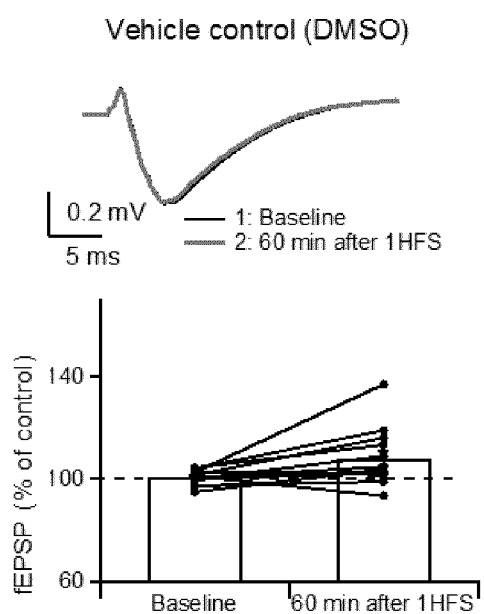
Figure 5A:
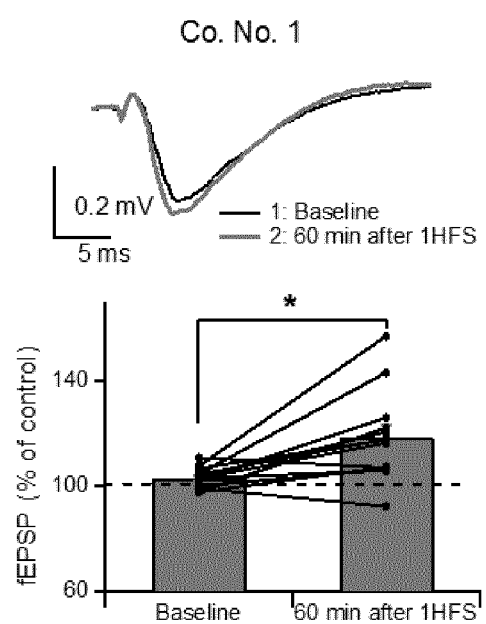
Figure 6A:
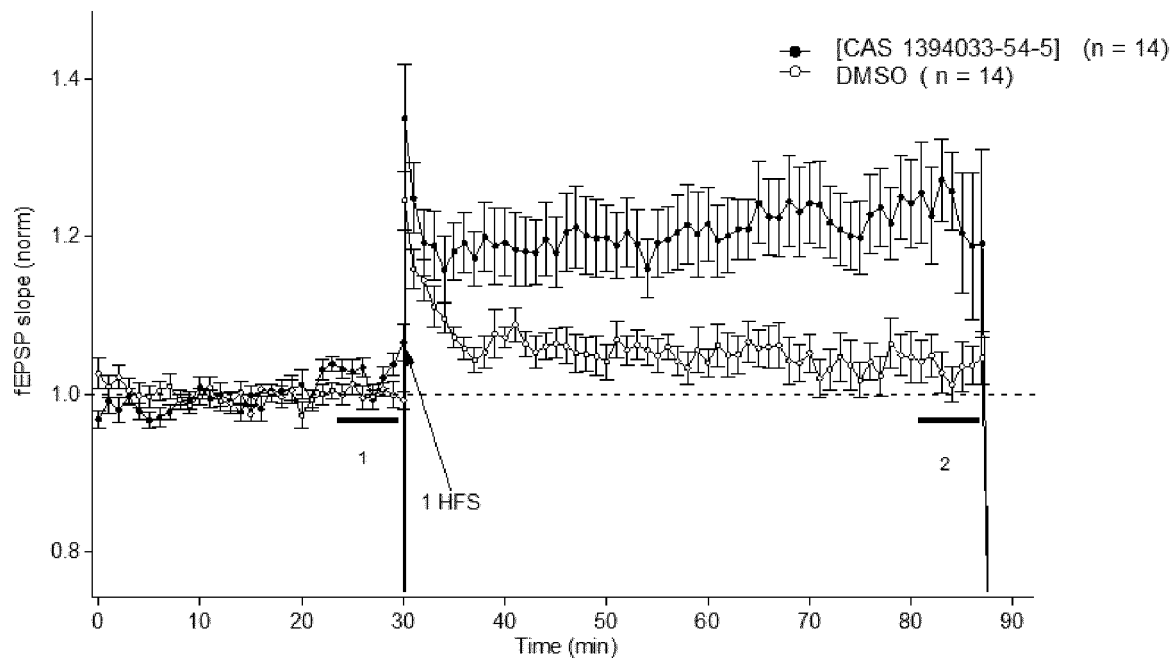
FIG. 6 shows the effect of [CAS 1394033-54-5] 1 on basal synaptic transmission at the mossy fiber synapse.
Figure 6A:
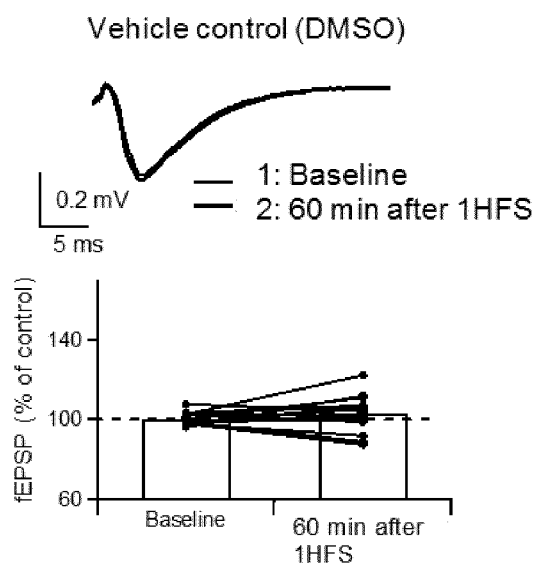
Figure 6A:
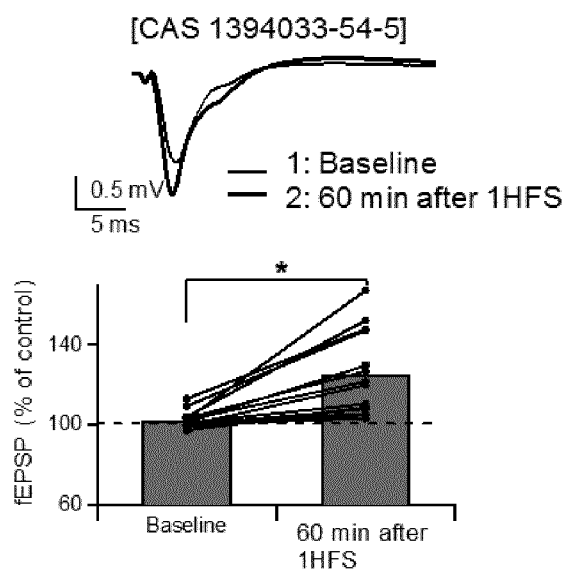

The results of this test are shown in FIGS. 3 and 4 for the effect of compound 1 on basal synaptic transmission and in FIG. 5 for the effect of compound 1 on the facilitation on induction of LTP with a weak Long Term Potentiation protocol. Interestingly, similar results were obtained with other PDE2 inhibitors such as 4-(1-azetidinyl)-7-methyl-5-[1-methyl-5-[5-(trifluoromethyl)-2-pyridinyl]-1H-pyrazol-4-yl]-imidazo[5,1-f][1,2,4]triazine [CAS 1394033-54-5] (WO2012114222, Pfizer) (see FIG. 6)

Single Dose PK/PD PDE2i Dog Study

For these studies male and female Marshall Beagle dogs (1-6 y) were used: 2 males and 2 females per treatment group. Cerebrospinal fluid (CSF) was sampled from the lateral ventricle via a needle guide cannula in instrumented conscious animals.

Figure 7:
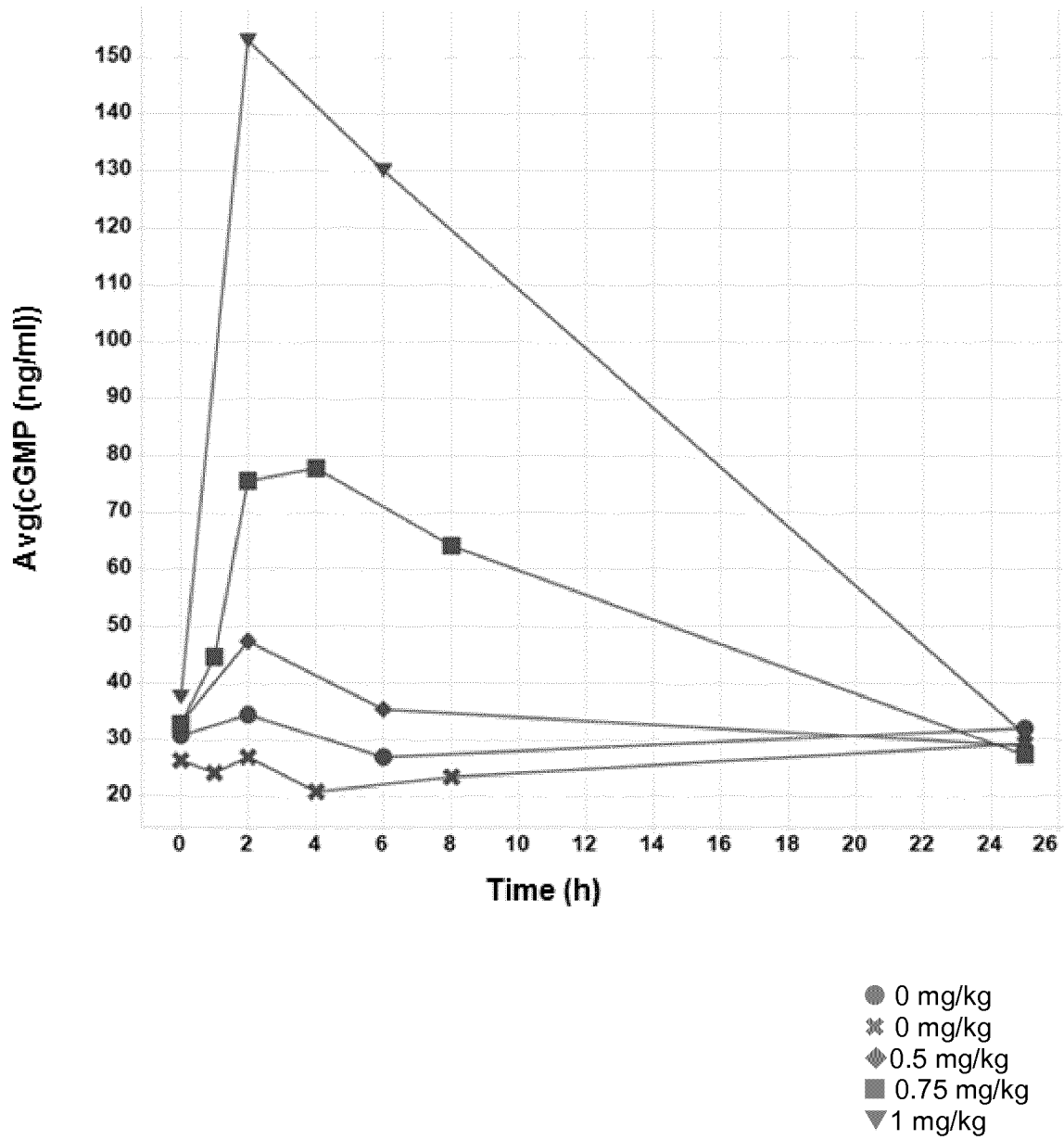
FIG. 7 shows measurement of cGMP levels in CSF in Marshall Beagle dogs.

Baseline CSF and blood samples were taken 2 to 5 days before dosing. The dogs are fasted overnight and the next morning dosed on an empty stomach (orally by gavage). At predetermined time points after dosing blood and/or CSF was collected for the measurement of compound levels and cGMP. Analysis of cGMP was done by LCMS/MS: 25 µl CSF was diluted with 125 µl artificial CSF (STIL (20 ng/ml)), centrifugated and 25 µl was injected. The systems used were: a Shimadzu SIL-30 UPLC-system (Hypercarb (50 mm×1 mm (3 µm)) column, basic (10 mM ammonium carbonate) aqueous-acetonitrile gradient (5% to 98% in 5.5 minutes) at a flow-rate of 250 µl/min) and an API Sciex 5500 system equiped with an ESI source (selective MRM transition (m/z 346.1→152.1 (75 msec dwelltime)). The results of this study are summarized in FIG. 7. After a single dose of compound 1 the following observations were made: slight to moderate tremors in 3/8 animals at 0.5 mg/kg; sedation and/or tremors in 6 out of 7 animals at 1 mg/kg (one animal was not dosed due to limited stock of the compound). Plasma pharmacokinetics showed a non-dose linearity. There was a dose related increase in cGMP in the CSF. Limited individual data in the vehicle group of PDE2 H-2 (n=2 at 1, 4 and 8 h) due to analytical errors.

PDE2 Inhibition Enhanced Synaptic Plasticity in Anesthetized Rats: Case Pilot Study with Compound 1

Introduction

Synaptic plasticity is a fundamental mechanism to many neurobiological functions. Long-term potentiation (LTP), a form of a long-lasting highly localized increase in synaptic strength in the hippocampus as well as in the cortex, is a synaptic substrate for memory and learning (Cooke and Bliss, Curr Opin Investig Drugs. 2005; 6(1): 25-34). The increase and decrease of synaptic strength depends on the activity of presynaptic and postsynaptic neurons, on how networks in the brain operate in setting up sensory representation of multiple items in the memory and producing appropriate motor response. Different features of these synaptic modifications, in intact brain, are crucial to the operation of different types of network and operations of several different brain circuit systems. Therefore, LTP is expected to be compromised in in aging psychiatric and neurodegenerative disorders such as Alzheimer's disease (Bergado and Almaguer, Neural Plast. 2002; 9(4):217-32; Rowan et al., Biochem Soc Trans. 2005; 33: 563-7). In animals, the procedure carried out under anesthesia in intact highly interconnected brain regions, provides a powerful tool to investigate lasting changes in effective connectivity and plasticity in hippocampal-cortex circuits following a tetanic electrical stimulation with low and high frequency delivered in single pulse or paired pulse (Albensi et al., Exp Neurol. 2007; 204:1-13). The studies help expand understanding of the neural circuits underlying development of impaired synaptic strength i.e. determine the direct-circuit path and the role of specific biological target harbored by a specific inter-regional network connections in mediating synaptic weakening. The procedure allows testing pharmacological agents aimed to restore the pathological forms of neuroplasticity e.g. reverse deficits in LTP and network connectivity by increasing synaptic efficacy, which is expected to have beneficial effects on related cognitive and learning ability (Cooke and Bliss, 2005; Albensi et al., 2007).

Phosphodiesterases (PDEs) are a class of enzymes responsible for metabolic inactivation of secondary messengers 3',5'-cyclic adenosine monophosphate (cAMP) and 3',5'-cyclic guanosine monophosphate (cGMP) (Francis et al. Physiol Rev. 2011, 9: 651-90). Up to 11 families of PDEs were categorized based on their structural, enzymatic and distribution (Omori and Kotera Circ Res. 2007; 100:309-27). The role of PDEs in the augmentation of cyclic nucleotide signaling makes these enzymes attractive targets for regulating excitability and enhancing the effects of neuronal communication. In the brain, PDE2 is mainly expressed in cortex, hippocampus and striatum where it controls the hydrolysis of cAMP. Over the last few years, research groups has focused on the development of PDE2 inhibitors as a way to modify intracellular second messengers, cGMP and cAMP to exert action on plasticity and cognitive processes (Duinen et al., Curr Pharm Des. 2015; 21:3813-28; Gomez and Breitenbucher, Bioorg Med Chem Lett. 2013; 23: 6522-7; Xu et al., Neurobiol Aging. 2015; 36:955-70; Barco et al., Expert Opin Ther Targets 2003; 7: 101-114).

In the present study, it was investigated whether PDE2 inhibition, using compound 1, leads to alterations in excitability or in ability to express synaptic potentiation in the dentate gyrus of anesthetized adult Sprague Dawley.

Material and Methods

Animals

The present experiments were conducted in strict accordance with the guidelines of the Association for Assessment and Accreditation of Laboratory Animal Care International (AAALAC), and with the European Communities Council Directive of 24 Nov. 1986 (86/609/EEC) and were approved by local ethical committee. Sprague Dawley rats weighing 170-200 g at the time of surgery) were group-housed in ventilated cages located on a 12-h light/dark cycle (lights on at 07:00 AM) after their arrival to animal facilities maintained under controlled environmental conditions.

Surgery and Electrophysiology

Rats were anesthetized with an intra-peritoneal injection of urethane 1.5 g/kg body weight. Animals were placed in a stereotactic frame for the insertion of electrodes and their body temperature was constantly monitored through a rectal probe and maintained at 37° C. with a heating pad. Supplementary administration of urethane (0.2-0.5 g/kg) was given when necessary to ensure full anesthesia. Two small holes (1 mm diameter) were drilled in the skull at the position of left hippocampus structures for stimulating and recording electrodes. A bipolar stimulating electrode; a pair of twisted stainless steel polyimide-coated wires with tips horizontally separated 0.125 µm apart (MS303/13-B. PlasticsOne), were positioned at the medial performant pathway (mPP) (AP −7.5, ML −3.8, DV −2.5), and a stainless coated recording electrode (MS303T-2-AIU, 0.008-0.005) are positioned at the Dentate Gyrus (DG) area of the dorsal hippocampus (AP −2.8, ML −3.8, DV −3.8). The dura was pierced through both holes, and the stimulating and recording electrodes were lowered very slowly (0.2 mm/min) through the cortex and upper layers of the hippocampus into the mPP and the DG of the dorsal hippocampus. During surgery all efforts were made to minimize animal suffering.

The field excitatory postsynaptic potential (fEPSP) slope is used as a measure of excitatory synaptic transmission. Single monophasic square 0.1 or 0.2 ms wave pulses generated by a constant current unit (MC, Germany) were applied for instance to the mPP and evoked responses are generated in the DG. Extracellular field potentials are amplified; band pass filtered between 1 Hz and 2 kHz, digitized and analyzed using custom made software. The electrodes were lowered until a negative deflecting fEPSP with the maximum response is observed. A minimum of 30 min is allowed to ensure stabilization excitability before measurements. Next, monophasic constant current pulses with stimulus intensities ranging from 50 to 500 µA were delivered to generate Input/Output (I/O) curves and determine the maximum PSA and fEPSP slopes, and then stimulus intensity that produced 50% of the maximum response (i.e., test pulse) was used in subsequent experiments.

LTP induction: Test stimulation was then applied every 5 min before and after tetanic stimulation. Responses were evoked by high frequency stimulation (10 stimulus trains of 20 square wave pulses, 0.2 ms duration at 200 Hz, 5 ms inter-stimulus interval, with 2 seconds inter-train interval). Five evoked responses were averaged for each time point measured during the experiments, half hour of baseline recording, immediately before drug application or tetanic stimulation (control for LTP induction). The magnitude of synaptic potentiation is expressed as the percentage of increase in the amplitude DG population spike (PSA), as well as fEPSP slope at the time interval after tetanic stimulation relative to the slopes averaged over the stable 30-min of the pharmacological period.

Responses at the selected pulse intensity were collected and averaged up to 130 min post-tetanization. The amplitude of the population spike was defined as the average of the amplitude from the first positive peak (a) to the first negative peak (b) and the amplitude from the negative peak (b) to the second positive peak (c): $[(a-b)/(c-b)]/2$. For quantification of the slope of fEPSPs, only very early component of the waveform (ΔV/Δt) was measured to avoid contamination by the population spike.

Histology

At the end of the electrophysiological study, electrical stimulation of 500 μA for 20 sec was delivered to produce a lesion at the end tip of the stimulation and recording electrodes and brains were harvested for histological verification of electrodes placement. Brain sections (20 mm) were examined using a light microscope. Animals with incorrect electrode placement were excluded from the study.

Drug

Compound 1 was dissolved in 10% Cyclodextrine (CD)+ 1HCl+NaCl for subcutaneous (SC) administration.

Statistic

For each animal, the stable baseline (pre-tetanus) responses over 30 min were averaged and the mean was normalized as being 100%, and the post-tetanus response data were expressed relative by the baseline average. Comparison of the effects of vehicle and compound 1 after tetanus was performed on 30 min intervals using one-way repeated-measures analysis of variance (ANOVA) on ranks followed by Iunnett's post hoc comparisons against baseline (100% values). Differences between treatments at discrete time points were examined using a two-tailed Student's t test. All statistical procedures were performed using StatExact Software.

Results

Figure 8A:
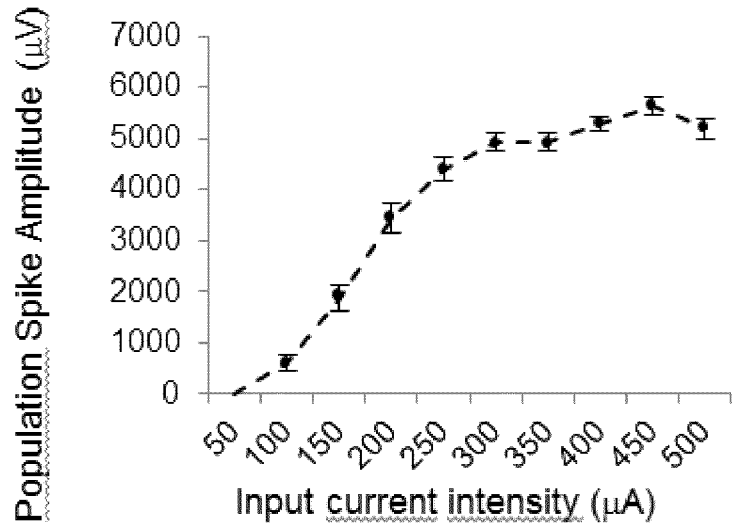
FIG. 8a shows Input-output curve for the slope of the field excitatory postsynaptic potential (fEPSP) recorded in the dentate gyrus; sample recordings showing mean population spike slope (PSA) responses at 30 min intervals.
Figure 8B:
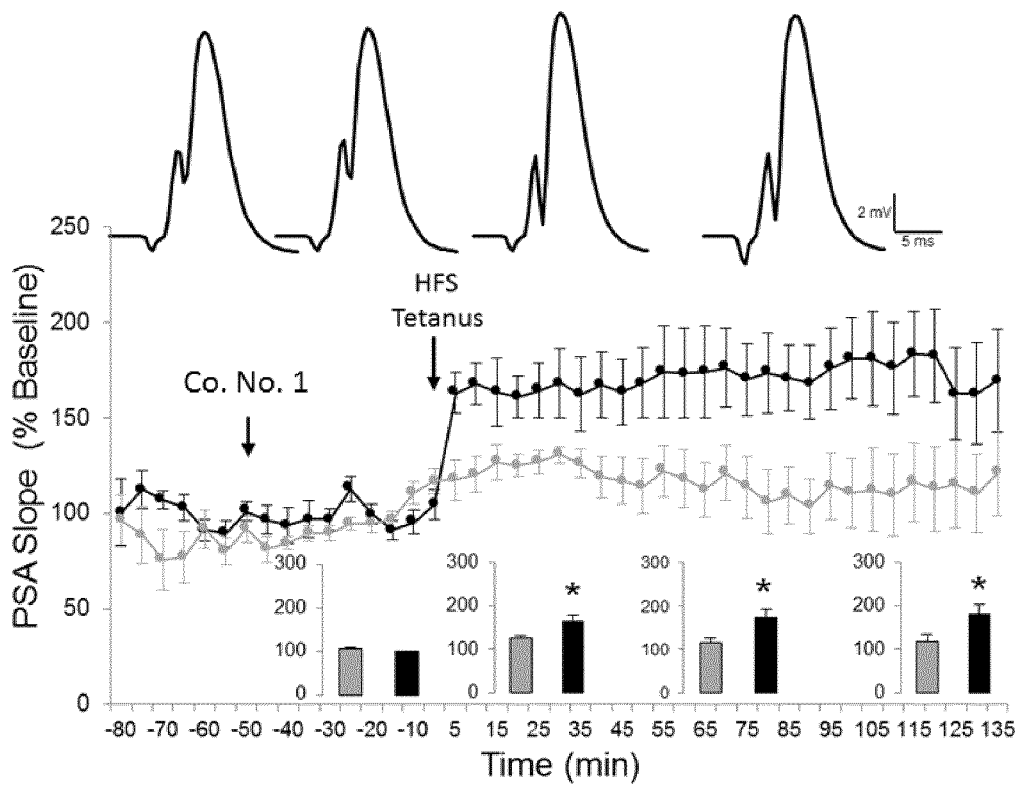
FIG. 8b shows LTP induced by high frequency stimulation (HFS) was enhanced by compound 1 at perforant path synapses as compared to vehicle condition; mean normalized PSA slope before and after HFS is plotted as a function of time; inset bar graphs show mean data over 30 min intervals before and after tetanization procedure.
Figure 8C:
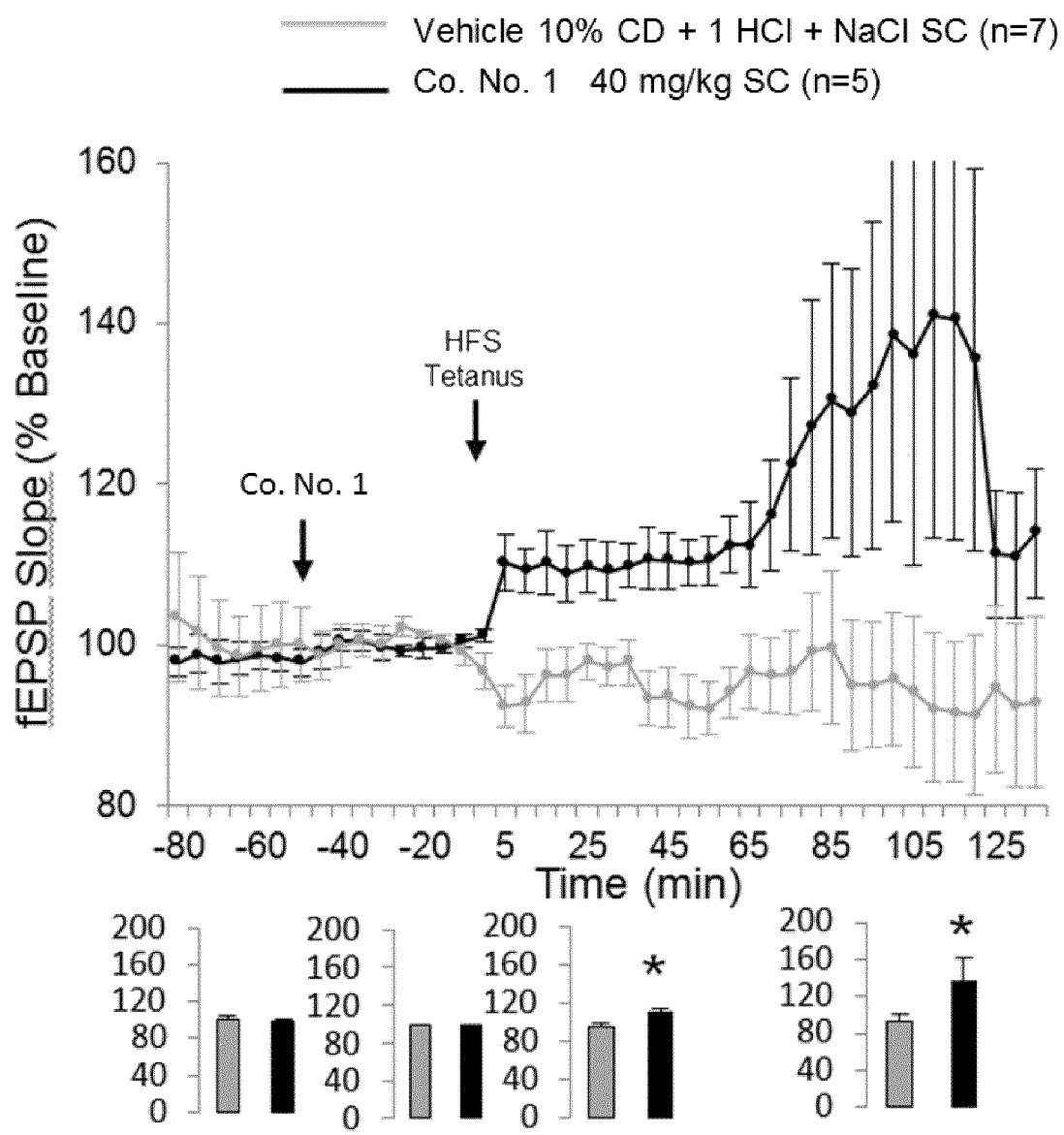
FIG. 8c shows lasting increases in the fEPSP slope. * $p<0.05$ compound 1 versus vehicle at each 30 min time intervals.

Basal synaptic transmission was not affected by compound 1 as no significant changes were found between vehicle-treated control during baseline pre-tetanus (FIG. 8b). During the LTP induction paradigm, subcutaneous administration of compound 1 (40 mg/kg) enhanced an enduring (>2 h) synaptic potentiation (FIG. 8b). At 0-30 min after completion of the tetanization, PSA slopes were 164±13% as compared to vehicle level 124±5%, p<0.05). At 90-120 min post-tetanization PSA amplitude was still higher (179±20% as compared to vehicle level 116±17%, p<0.05). Similarly, analysis of stimulus-response curves revealed a significant lasting increase in the fEPSP slope as compared to vehicle condition (90-120 min: 137±24% as compared to vehicle level 94±7%, p<0.05) (FIG. 8c).

Overall, compound 1 facilitates LTP in vivo, but does not affect basal synaptic transmission.

Prophetic Composition Examples

"Active ingredient" as used throughout these examples relates to compound 1, a pharmaceutically acceptable salt thereof, or a solvate thereof.

Typical examples of recipes for the formulation of the invention are as follows:

1. Tablets

| | |
|---|---|
| Compound 1 | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each 1 milliliter contains 1 to 5 mg of one of compound 1, 50 mg of sodium carboxymethyl cellulose, 1 mg of sodium benzoate, 500 mg of sorbitol and water ad 1 ml.

3. Injectable

A parenteral composition is prepared by stirring 1.5% by weight of compound 1 of the invention in 10% by volume propylene glycol in water.

4. Ointment

| | |
|---|---|
| Compound 1 | 5 to 1000 mg |
| Stearyl alcohol | 3 g |
| Lanoline | 5 g |
| White petroleum | 15 g |
| Water | ad 100 g |

Reasonable variations are not to be regarded as a departure from the scope of the invention. It will be obvious that the thus described invention may be varied in many ways by those skilled in the art.

The invention claimed is:

1. A compound having the formula (1)

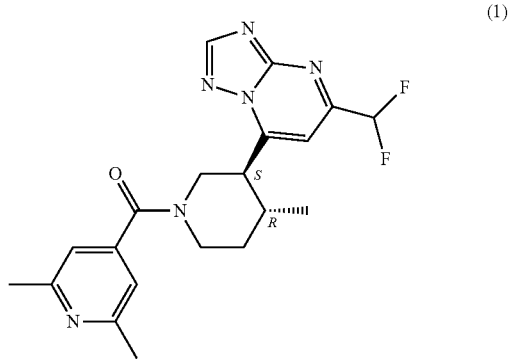

(1)

or a pharmaceutically acceptable salt or a solvate thereof.

2. The hydrochloride salt of the compound of formula (1) according to claim 1.

3. A pharmaceutical composition comprising a therapeutically effective amount of the compound of claim 1 and a pharmaceutically acceptable carrier.

4. A pharmaceutical composition comprising a therapeutically effective amount of the compound of claim 2 and a pharmaceutically acceptable carrier.

5. A method of treatment comprising administering to a patient in need of treatment for a central nervous system disorder selected from the group of Alzheimer's disease; stroke; a learning disorder; a disorder or condition comprising as a symptom a deficiency in attention and/or cognition; mild cognitive impairment; age-related cognitive impairment; cognitive impairment related to perception, concentration, learning or memory; and memory disorders, a therapeutically effective amount of a compound having the formula (1)

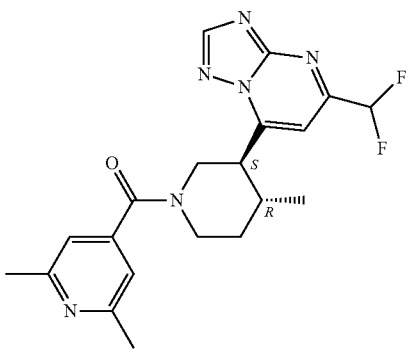

(1)

or a pharmaceutically acceptable salt or a solvate thereof.

6. The method of claim 5, wherein the central nervous system disorder is Alzheimer's disease.

7. A process for preparing a pharmaceutical composition comprising mixing a pharmaceutically acceptable carrier intimately with a therapeutically effective amount of a compound of claim 1.

8. The method of claim 5 wherein an additional pharmaceutical agent is used in the treatment of said central nervous system disorder.

9. The method of claim 5 wherein the central nervous system disorder is disorders or conditions comprising as a symptom a deficiency in attention and/or cognition.

10. The method of claim 9 wherein the disorder or condition is selected from the group consisting of dementia associated with Alzheimer's disease; attention-deficit/hyperactivity disorder (ADHD); mild cognitive impairment; age-related cognitive impairment; and cognitive impairment related to perception, concentration, learning and memory.

11. The method of claim 10 wherein the disorder or condition is dementia associated with Alzheimer's disease.

* * * * *